(12) United States Patent
Petrosenko et al.

(10) Patent No.: US 7,896,856 B2
(45) Date of Patent: Mar. 1, 2011

(54) WOUND PACKING FOR PREVENTING WOUND CLOSURE

(76) Inventors: Robert Petrosenko, Batesville, IN (US); Kevin L. Wilkinson, Batesville, IN (US)

( * ) Notice: Subject to any disclaimer, the term of this patent is extended or adjusted under 35 U.S.C. 154(b) by 418 days.

(21) Appl. No.: 10/524,957

(22) PCT Filed: Dec. 20, 2002

(86) PCT No.: PCT/US02/41234
§ 371 (c)(1),
(2), (4) Date: Feb. 18, 2005

(87) PCT Pub. No.: WO2004/018020
PCT Pub. Date: Mar. 4, 2004

(65) Prior Publication Data
US 2006/0041247 A1    Feb. 23, 2006

Related U.S. Application Data

(60) Provisional application No. 60/405,010, filed on Aug. 21, 2002.

(51) Int. Cl.
*A61M 1/00* (2006.01)
*A61F 13/00* (2006.01)
*A61F 15/00* (2006.01)

(52) U.S. Cl. .......... 604/313; 604/304; 604/305; 602/41; 602/42

(58) Field of Classification Search .................. 604/289, 604/304, 305, 307, 308, 313, 315–318, 327, 604/328, 540, 544; 602/41–43, 47, 59; 601/6–14
See application file for complete search history.

(56) References Cited

U.S. PATENT DOCUMENTS

| | | |
|---|---|---|
| 774,529 A | 11/1904 | Nieschang |
| 1,000,001 A | 8/1911 | Holz |
| 1,355,846 A | 10/1920 | Rannells |
| 1,385,346 A | 7/1921 | Taylor |
| 1,709,520 A | 4/1929 | Chandler |
| 1,936,129 A | 11/1933 | Fisk |
| 2,078,180 A | 4/1937 | Kronenberg |
| 2,195,771 A | 4/1940 | Estler |
| 2,221,758 A | 11/1940 | Elmquist |
| 2,305,289 A | 12/1942 | Coburg .......... 128/132 |
| 2,338,339 A | 1/1944 | LaMere et al. |
| 2,443,481 A | 6/1948 | Sene |
| 2,547,758 A | 4/1951 | Keeling .......... 128/349 |
| 2,560,915 A | 7/1951 | Bamberger .......... 128/350 |
| 2,573,791 A | 11/1951 | Howells |

(Continued)

FOREIGN PATENT DOCUMENTS

AU    550575 A1    8/1982

(Continued)

OTHER PUBLICATIONS

Davydov, et al., Vestn. Khir., Sep. 1988—"Vacuum Therapy in the Treatment of Acute Suppurative Diseases Of Soft Tissues and Suppurative Wounds" (English translation by R. McElroy Translation Co., Austin, Texas).

(Continued)

*Primary Examiner* — Melanie J Hand

(57) ABSTRACT

A wound insert or wound packing for preventing wound closure is provided. Such packing may be used alone or in regular bandages or in vacuum bandages or in irrigation bandages. Some illustrative wound inserts are configured for placement within an undermined portion or a tunneled portion of a wound.

22 Claims, 8 Drawing Sheets

U.S. PATENT DOCUMENTS

| | | | |
|---|---|---|---|
| 2,577,945 A | 12/1951 | Atherton | |
| 2,632,443 A | 3/1953 | Lesher | |
| 2,682,873 A | 7/1954 | Evans et al. | |
| 2,910,763 A | 11/1959 | Lauterbach | 128/72.2 |
| 2,969,057 A | 1/1961 | Simmons | 128/2 |
| 3,026,874 A | 3/1962 | Stevens | |
| 3,066,672 A | 12/1962 | Crosby, Jr. et al. | 128/276 |
| 3,315,665 A | 4/1967 | MacLeod | |
| 3,367,332 A | 2/1968 | Groves | |
| 3,382,867 A | 5/1968 | Reaves | |
| 3,430,631 A | 3/1969 | Abramson | 128/350 |
| 3,492,991 A | 2/1970 | Dyer, Jr. | |
| 3,520,300 A | 7/1970 | Flower, Jr. | |
| 3,528,416 A | 9/1970 | Chamberlain | |
| 3,568,675 A | 3/1971 | Harvey | |
| 3,585,742 A | 6/1971 | Tyler | |
| 3,599,639 A | 8/1971 | Spotz | |
| 3,610,238 A | 10/1971 | Rich, Jr. | |
| 3,623,087 A | 11/1971 | Gallichotte | |
| 3,648,692 A | 3/1972 | Wheeler | |
| 3,682,180 A | 8/1972 | McFarlane | 128/350 |
| 3,683,894 A | 8/1972 | Villari | |
| 3,721,244 A | 3/1973 | Elmaleh | |
| 3,752,158 A | 8/1973 | Kariher | |
| 3,753,439 A | 8/1973 | Brugarolas et al. | 128/350 |
| 3,782,377 A | 1/1974 | Rychlik | |
| 3,812,972 A | 5/1974 | Rosenblum | |
| 3,814,095 A | 6/1974 | Lubens | |
| 3,823,720 A | 7/1974 | Tribble | 128/350 |
| 3,826,254 A | 7/1974 | Mellor | 128/133 |
| 3,831,588 A | 8/1974 | Rindner | |
| 3,860,008 A * | 1/1975 | Miner et al. | 604/93.01 |
| 3,874,387 A | 4/1975 | Barbieri | |
| 3,903,882 A | 9/1975 | Augurt | |
| 3,924,624 A | 12/1975 | Schachet | 128/276 |
| 3,935,863 A | 2/1976 | Kliger | |
| 3,954,105 A | 5/1976 | Nordby et al. | |
| 3,982,546 A | 9/1976 | Friend | |
| 4,004,590 A | 1/1977 | Muriot | |
| 4,013,076 A | 3/1977 | Puderbaugh et al. | |
| RE29,319 E | 7/1977 | Nordby et al. | |
| RE29,321 E | 7/1977 | Holbrook | |
| 4,058,123 A | 11/1977 | May | 128/278 |
| 4,080,970 A | 3/1978 | Miller | |
| 4,096,853 A | 6/1978 | Weigand | 128/2 |
| 4,112,947 A | 9/1978 | Nehring | |
| 4,139,004 A | 2/1979 | Gonzalez, Jr. | |
| 4,149,541 A | 4/1979 | Gammons et al. | |
| 4,165,748 A | 8/1979 | Johnson | 128/348 |
| 4,178,974 A | 12/1979 | Levin | |
| 4,184,510 A | 1/1980 | Murry et al. | 137/565 |
| 4,191,204 A | 3/1980 | Nehring | |
| 4,219,021 A | 8/1980 | Fink | 128/214 |
| 4,224,941 A | 9/1980 | Stivala | |
| 4,233,969 A | 11/1980 | Lock et al. | 128/156 |
| 4,245,630 A | 1/1981 | Lloyd et al. | 128/155 |
| 4,250,882 A | 2/1981 | Adair | |
| 4,256,109 A | 3/1981 | Nichols | 128/276 |
| 4,261,363 A | 4/1981 | Russo | 128/350 |
| 4,275,721 A | 6/1981 | Olson | |
| 4,284,079 A | 8/1981 | Adair | 128/295 |
| 4,297,995 A | 11/1981 | Golub | |
| 4,333,468 A | 6/1982 | Geist | 128/348 |
| 4,341,209 A | 7/1982 | Schaar | |
| 4,364,394 A | 12/1982 | Wilkinson | 604/96 |
| 4,373,519 A | 2/1983 | Errede et al. | |
| 4,382,441 A | 5/1983 | Svedman | |
| 4,392,853 A | 7/1983 | Muto | 604/171 |
| 4,392,858 A | 7/1983 | George et al. | 604/187 |
| 4,399,816 A | 8/1983 | Spangler | |
| 4,419,097 A | 12/1983 | Rowland | 604/174 |
| 4,445,897 A | 5/1984 | Ekbladh et al. | 604/280 |
| 4,457,755 A | 7/1984 | Wilson | |
| 4,460,370 A | 7/1984 | Allison et al. | |
| 4,465,062 A | 8/1984 | Versaggi et al. | |
| 4,465,485 A | 8/1984 | Kashmer et al. | 604/320 |
| 4,469,092 A | 9/1984 | Marshall et al. | |
| 4,475,909 A | 10/1984 | Eisenberg | 604/349 |
| 4,480,638 A | 11/1984 | Schmid | 128/155 |
| 4,508,533 A | 4/1985 | Abramson | 604/35 |
| 4,525,156 A | 6/1985 | Benusa et al. | 604/28 |
| 4,525,166 A | 6/1985 | Leclerc | |
| 4,525,374 A | 6/1985 | Vaillancourt | 427/2 |
| 4,533,352 A | 8/1985 | Van Beek et al. | |
| 4,533,419 A | 8/1985 | Pieslak et al. | |
| 4,540,412 A | 9/1985 | Van Overloop | |
| 4,543,100 A | 9/1985 | Brodsky | 604/180 |
| 4,548,202 A | 10/1985 | Duncan | 128/334 |
| 4,551,139 A | 11/1985 | Plaas et al. | 604/290 |
| 4,553,967 A | 11/1985 | Ferguson et al. | |
| 4,569,348 A | 2/1986 | Hasslinger | 604/179 |
| 4,569,674 A | 2/1986 | Phillips et al. | |
| 4,573,965 A | 3/1986 | Russo | |
| 4,579,555 A | 4/1986 | Russo | |
| 4,596,564 A | 6/1986 | Spetzler et al. | 604/281 |
| 4,605,399 A | 8/1986 | Weston et al. | |
| 4,608,041 A | 8/1986 | Nielsen | |
| 4,614,794 A | 9/1986 | Easton et al. | 530/356 |
| 4,624,656 A | 11/1986 | Clark et al. | |
| 4,633,863 A | 1/1987 | Filips et al. | |
| 4,637,819 A | 1/1987 | Ouellette et al. | |
| 4,640,688 A | 2/1987 | Hauser | 604/352 |
| 4,641,643 A | 2/1987 | Greer | |
| 4,645,492 A | 2/1987 | Weeks | |
| 4,655,210 A | 4/1987 | Edenbaum et al. | |
| 4,655,754 A | 4/1987 | Richmond et al. | |
| 4,661,093 A | 4/1987 | Beck et al. | |
| 4,664,652 A | 5/1987 | Weilbacher | |
| 4,664,662 A | 5/1987 | Webster | |
| 4,667,666 A | 5/1987 | Fryslie | |
| 4,679,590 A | 7/1987 | Hergenroeder | |
| 4,704,102 A | 11/1987 | Guthery | 604/28 |
| 4,710,165 A | 12/1987 | McNeil et al. | 604/67 |
| 4,713,051 A | 12/1987 | Steppe et al. | 604/30 |
| 4,717,332 A | 1/1988 | Edens | 431/8 |
| 4,717,379 A | 1/1988 | Ekholmer | 604/43 |
| 4,717,382 A | 1/1988 | Clemens et al. | |
| 4,733,659 A | 3/1988 | Edenbaum et al. | |
| 4,735,606 A | 4/1988 | Davison | |
| 4,735,610 A | 4/1988 | Akkas et al. | |
| 4,740,202 A | 4/1988 | Stacey et al. | |
| 4,743,232 A | 5/1988 | Kruger | |
| 4,747,166 A | 5/1988 | Kuntz | |
| 4,758,220 A | 7/1988 | Sundblom et al. | 604/65 |
| 4,759,354 A | 7/1988 | Quarfoot | |
| 4,765,316 A | 8/1988 | Marshall | |
| 4,778,446 A | 10/1988 | Jensen | |
| 4,778,456 A | 10/1988 | Lokken | |
| 4,787,888 A | 11/1988 | Fox | 604/20 |
| 4,798,578 A | 1/1989 | Ranford | |
| 4,820,265 A | 4/1989 | DeSatnick et al. | |
| 4,820,284 A | 4/1989 | Hauri | |
| 4,826,494 A | 5/1989 | Richmond et al. | 604/323 |
| 4,826,949 A | 5/1989 | Stanko | 528/272 |
| 4,834,110 A | 5/1989 | Richard | |
| 4,838,883 A | 6/1989 | Matsuura | 604/349 |
| 4,840,187 A | 6/1989 | Brazier | 128/844 |
| 4,841,962 A | 6/1989 | Berg et al. | 128/156 |
| 4,850,350 A | 7/1989 | Jackson | 128/207.16 |
| 4,863,449 A | 9/1989 | Therriault et al. | 604/352 |
| 4,872,450 A | 10/1989 | Austad | |
| 4,878,901 A | 11/1989 | Sachse | 604/174 |
| 4,890,608 A | 1/1990 | Steer | |
| 4,897,081 A | 1/1990 | Poirier et al. | |
| 4,900,302 A | 2/1990 | Newton | 604/30 |
| 4,902,508 A | 2/1990 | Badylak et al. | 424/95 |
| 4,906,233 A | 3/1990 | Moriuchi et al. | 604/174 |
| 4,906,240 A | 3/1990 | Reed et al. | |
| 4,915,694 A | 4/1990 | Yamamoto et al. | |
| 4,917,112 A | 4/1990 | Kalt | |
| 4,919,654 A | 4/1990 | Kalt | 604/180 |
| 4,921,492 A | 5/1990 | Schultz et al. | |
| 4,930,997 A | 6/1990 | Bennett | |
| 4,941,882 A | 7/1990 | Ward et al. | |
| 4,950,230 A | 8/1990 | Kendell | 604/28 |
| 4,953,565 A | 9/1990 | Tachibana et al. | |
| 4,956,178 A | 9/1990 | Badylak et al. | 424/551 |

| Patent | Date | Inventor | Ref |
|---|---|---|---|
| 4,957,492 A | 9/1990 | McVay | |
| 4,962,761 A | 10/1990 | Golden | |
| 4,969,880 A | 11/1990 | Zamierowski | |
| 4,969,881 A | 11/1990 | Viesturs | |
| 4,970,298 A | 11/1990 | Silver et al. | 530/356 |
| 4,985,019 A | 1/1991 | Michelson | 604/180 |
| 4,988,336 A | 1/1991 | Kohn | |
| 4,990,144 A | 2/1991 | Blott | |
| 4,991,574 A | 2/1991 | Pocknell | |
| 4,994,022 A | 2/1991 | Steffler et al. | |
| 4,997,425 A | 3/1991 | Shioya et al. | |
| 5,000,172 A | 3/1991 | Ward | |
| 5,000,741 A | 3/1991 | Kalt | |
| 5,002,528 A | 3/1991 | Palestrant | |
| 5,002,529 A | 3/1991 | Cunningham | |
| 5,003,971 A | 4/1991 | Buckley | |
| 5,014,389 A | 5/1991 | Ogilvie et al. | |
| 5,034,003 A | 7/1991 | Denance | |
| 5,034,006 A | 7/1991 | Hosoda et al. | |
| 5,035,865 A | 7/1991 | Inaba et al. | |
| 5,037,397 A | 8/1991 | Kalt et al. | 604/174 |
| 5,042,978 A | 8/1991 | Quenin et al. | |
| 5,045,777 A | 9/1991 | Itagaki | |
| 5,060,662 A | 10/1991 | Farnswoth, III | |
| 5,071,409 A | 12/1991 | Rosenberg | |
| 5,073,172 A | 12/1991 | Fell | |
| 5,080,650 A * | 1/1992 | Hirsch et al. | 604/104 |
| 5,086,170 A | 2/1992 | Luheshi et al. | 540/303 |
| 5,086,763 A | 2/1992 | Hathman | |
| 5,086,764 A | 2/1992 | Gilman | |
| 5,092,858 A | 3/1992 | Benson et al. | 604/319 |
| 5,100,395 A | 3/1992 | Rosenberg | 604/284 |
| 5,100,396 A | 3/1992 | Zamierowski | |
| 5,101,808 A | 4/1992 | Kobayashi et al. | |
| 5,106,362 A | 4/1992 | Gilman | |
| 5,106,629 A | 4/1992 | Cartmell et al. | |
| 5,108,364 A | 4/1992 | Takezawa et al. | 604/43 |
| 5,134,994 A | 8/1992 | Say | 128/200.24 |
| 5,135,518 A | 8/1992 | Vera | |
| 5,146,925 A | 9/1992 | Snow | |
| 5,147,338 A | 9/1992 | Lang et al. | |
| 5,149,331 A | 9/1992 | Ferdman et al. | |
| 5,152,757 A | 10/1992 | Eriksson | |
| 5,160,322 A | 11/1992 | Scheremet et al. | |
| 5,167,613 A | 12/1992 | Karami et al. | |
| 5,167,622 A | 12/1992 | Muto | 604/35 |
| 5,170,781 A | 12/1992 | Loomis | |
| 5,176,502 A | 1/1993 | Sanderson et al. | |
| 5,176,663 A | 1/1993 | Svedman et al. | |
| 5,176,667 A | 1/1993 | DeBring | |
| 5,181,908 A | 1/1993 | Bell | 604/24 |
| 5,189,609 A | 2/1993 | Tivig et al. | |
| 5,197,948 A | 3/1993 | Ghodsian | 604/30 |
| 5,215,522 A | 6/1993 | Page et al. | 604/33 |
| 5,215,539 A | 6/1993 | Schoolman | |
| 5,224,929 A | 7/1993 | Remiszewski | 604/30 |
| 5,228,431 A | 7/1993 | Giarretto | |
| 5,230,350 A | 7/1993 | Fentress | |
| 5,232,453 A | 8/1993 | Plass et al. | 604/180 |
| 5,238,654 A | 8/1993 | Nohl et al. | |
| 5,249,121 A | 9/1993 | Baum et al. | |
| 5,256,418 A | 10/1993 | Kemp et al. | 424/423 |
| 5,261,893 A | 11/1993 | Zamierowski | |
| 5,263,922 A | 11/1993 | Sova et al. | |
| 5,265,605 A | 11/1993 | Afflerbach | |
| 5,275,826 A | 1/1994 | Badylak et al. | 424/551 |
| 5,278,100 A | 1/1994 | Doan et al. | 437/200 |
| 5,279,550 A | 1/1994 | Habib et al. | 604/38 |
| 5,281,422 A | 1/1994 | Badylak et al. | 424/551 |
| 5,291,887 A | 3/1994 | Stanley et al. | |
| 5,298,015 A | 3/1994 | Komatsuzaki et al. | |
| 5,306,298 A | 4/1994 | Godley, III et al. | |
| 5,314,409 A | 5/1994 | Sarosiek et al. | 604/101 |
| 5,330,452 A | 7/1994 | Zook | |
| 5,335,651 A | 8/1994 | Foster et al. | |
| 5,338,293 A | 8/1994 | Jeppsson et al. | 604/29 |
| 5,342,293 A | 8/1994 | Zanger | |
| 5,342,301 A | 8/1994 | Saab | 604/96 |
| 5,342,376 A | 8/1994 | Ruff | 606/151 |
| 5,344,415 A | 9/1994 | DeBusk et al. | |
| 5,349,965 A | 9/1994 | McCarver | |
| 5,352,463 A | 10/1994 | Badylak et al. | 424/551 |
| 5,358,494 A | 10/1994 | Svedman | |
| 5,370,610 A | 12/1994 | Reynolds | 604/43 |
| 5,372,821 A | 12/1994 | Badylak et al. | 424/551 |
| 5,374,254 A | 12/1994 | Buma | |
| 5,376,252 A | 12/1994 | Ekstrom et al. | |
| 5,380,280 A | 1/1995 | Peterson | |
| 5,395,315 A | 3/1995 | Griep | |
| 5,409,013 A | 4/1995 | Clement | 128/753 |
| 5,413,788 A | 5/1995 | Edwards et al. | |
| 5,419,768 A | 5/1995 | Kayser | |
| 5,431,622 A | 7/1995 | Pyrozyk et al. | |
| 5,437,622 A | 8/1995 | Carion | 602/57 |
| 5,437,651 A | 8/1995 | Todd et al. | |
| 5,445,604 A | 8/1995 | Lang | |
| 5,445,833 A | 8/1995 | Badylak et al. | 424/551 |
| 5,447,505 A | 9/1995 | Valentine et al. | |
| 5,449,383 A | 9/1995 | Chatelier et al. | 623/1 |
| 5,451,215 A | 9/1995 | Wolter | |
| 5,451,373 A | 9/1995 | Lewis et al. | |
| 5,478,333 A | 12/1995 | Asherman, Jr. | |
| 5,484,420 A | 1/1996 | Russo | |
| 5,484,427 A | 1/1996 | Gibbons | |
| 5,484,428 A | 1/1996 | Drainville et al. | |
| 5,487,889 A | 1/1996 | Eckert et al. | |
| 5,516,533 A | 5/1996 | Badylak et al. | 424/551 |
| 5,520,652 A | 5/1996 | Peterson | |
| 5,527,293 A | 6/1996 | Zamierowski | |
| 5,531,670 A | 7/1996 | Westby et al. | |
| 5,533,981 A | 7/1996 | Mandro et al. | |
| 5,534,346 A | 7/1996 | Robinson | |
| 5,540,668 A | 7/1996 | Wilson, Jr. et al. | 604/248 |
| 5,542,918 A | 8/1996 | Atkinson | |
| 5,549,584 A | 8/1996 | Gross | |
| 5,554,389 A | 9/1996 | Badylak et al. | 424/558 |
| 5,556,375 A | 9/1996 | Ewall | |
| 5,558,639 A | 9/1996 | Gangemi et al. | |
| 5,573,784 A | 11/1996 | Badylak et al. | 424/551 |
| 5,578,022 A | 11/1996 | Scherson et al. | |
| 5,578,662 A | 11/1996 | Bennett et al. | 524/54 |
| 5,607,388 A | 3/1997 | Ewall | |
| 5,621,035 A | 4/1997 | Lyles et al. | 524/404 |
| 5,624,418 A | 4/1997 | Shepard | |
| 5,628,735 A | 5/1997 | Skow | |
| 5,629,186 A | 5/1997 | Yasukawa et al. | 435/177 |
| 5,631,011 A | 5/1997 | Wadström | 424/400 |
| 5,635,201 A | 6/1997 | Fabo | |
| 5,636,643 A | 6/1997 | Argenta et al. | |
| 5,641,518 A | 6/1997 | Badylak et al. | 424/551 |
| 5,645,081 A | 7/1997 | Argenta et al. | |
| 5,645,860 A | 7/1997 | Knapp et al. | 424/551 |
| 5,655,258 A | 8/1997 | Heintz | |
| 5,656,027 A | 8/1997 | Ellingboe | |
| 5,662,598 A | 9/1997 | Tobin | |
| 5,662,624 A | 9/1997 | Sundstrom et al. | |
| 5,662,625 A | 9/1997 | Westwood | |
| 5,669,892 A | 9/1997 | Keogh et al. | |
| 5,672,151 A | 9/1997 | Calderon-Garciduenas | 602/21 |
| 5,672,152 A | 9/1997 | Mason et al. | |
| 5,674,193 A | 10/1997 | Hayes | 604/28 |
| 5,678,564 A | 10/1997 | Lawrence et al. | |
| 5,681,290 A | 10/1997 | Alexander | 604/180 |
| 5,690,815 A | 11/1997 | Krasnoff et al. | |
| 5,695,998 A | 12/1997 | Badylak et al. | 435/391 |
| 5,697,920 A | 12/1997 | Gibbons | |
| 5,711,969 A | 1/1998 | Patel et al. | 424/551 |
| 5,718,955 A | 2/1998 | McGuire et al. | |
| 5,735,833 A | 4/1998 | Olson | |
| 5,741,237 A | 4/1998 | Walker | |
| 5,749,842 A | 5/1998 | Cheong et al. | 602/41 |
| 5,753,267 A | 5/1998 | Badylak et al. | 424/551 |
| 5,755,791 A | 5/1998 | Whitson et al. | 623/15 |
| 5,759,570 A | 6/1998 | Arnold | |
| 5,762,640 A | 6/1998 | Kajiwara et al. | |
| 5,762,966 A | 6/1998 | Knapp et al. | 424/551 |
| 5,780,281 A | 7/1998 | Yasukawa et al. | 435/176 |
| 5,782,871 A | 7/1998 | Fujiwara et al. | |

| | | | |
|---|---|---|---|
| 5,795,584 A | 8/1998 | Totakura et al. ............... 424/426 |
| 5,800,383 A | 9/1998 | Chandler et al. ................. 604/35 |
| 5,817,145 A | 10/1998 | Augustine et al. |
| 5,827,246 A | 10/1998 | Bowen |
| 5,827,296 A | 10/1998 | Morris et al. |
| 5,855,619 A | 1/1999 | Caplan et al. .................... 623/11 |
| 5,866,414 A | 2/1999 | Badylak et al. ............... 435/325 |
| 5,881,723 A | 3/1999 | Wallace et al. |
| 5,891,111 A | 4/1999 | Ismael .......................... 604/280 |
| 5,902,874 A | 5/1999 | Roby et al. .................... 528/310 |
| 5,902,875 A | 5/1999 | Roby et al. .................... 528/310 |
| 5,911,222 A | 6/1999 | Lawrence et al. |
| 5,914,387 A | 6/1999 | Roby et al. .................... 528/310 |
| 5,919,476 A | 7/1999 | Fischer et al. |
| 5,921,972 A | 7/1999 | Skow |
| 5,928,174 A | 7/1999 | Gibbins |
| 5,931,304 A | 8/1999 | Hammond .................... 206/570 |
| 5,941,859 A | 8/1999 | Lerman |
| 5,942,496 A | 8/1999 | Bonadio et al. ................. 514/44 |
| 5,947,914 A | 9/1999 | Augustine |
| 5,951,295 A | 9/1999 | Lyles et al. ................. 433/228.1 |
| 5,954,680 A | 9/1999 | Augustine |
| 5,961,480 A | 10/1999 | Augustine |
| 5,962,427 A | 10/1999 | Goldstein et al. ............... 514/44 |
| 5,964,721 A | 10/1999 | Augustine |
| 5,964,723 A | 10/1999 | Augustine |
| 5,986,163 A | 11/1999 | Augustine |
| 5,997,568 A | 12/1999 | Liu ............................... 606/228 |
| 6,010,527 A | 1/2000 | Augustine et al. |
| 6,013,048 A | 1/2000 | Podany et al. ................... 604/22 |
| 6,017,493 A | 1/2000 | Cambron et al. |
| 6,039,724 A | 3/2000 | Seifert et al. |
| 6,045,518 A | 4/2000 | Augustine |
| 6,045,541 A | 4/2000 | Matsumoto et al. |
| 6,051,747 A | 4/2000 | Lindquist et al. |
| 6,056,730 A | 5/2000 | Greter |
| 6,071,254 A | 6/2000 | Augustine |
| 6,071,267 A | 6/2000 | Zamierowski |
| 6,071,304 A | 6/2000 | Augustine et al. |
| 6,080,189 A | 6/2000 | Augustine et al. |
| 6,080,243 A | 6/2000 | Insley et al. |
| 6,093,160 A | 7/2000 | Augustine et al. |
| 6,093,230 A | 7/2000 | Johnson, III et al. |
| 6,095,992 A | 8/2000 | Augustine |
| 6,099,567 A | 8/2000 | Badylak et al. .................. 623/13 |
| 6,110,197 A | 8/2000 | Augustine et al. |
| 6,113,561 A | 9/2000 | Augustine |
| 6,117,111 A | 9/2000 | Fleischmann |
| 6,135,116 A | 10/2000 | Vogel et al. |
| 6,142,982 A | 11/2000 | Hunt et al. |
| 6,143,945 A | 11/2000 | Augustine et al. |
| 6,149,614 A | 11/2000 | Dunshee et al. |
| 6,171,344 B1 | 1/2001 | Atala ......................... 623/23.64 |
| 6,174,306 B1 | 1/2001 | Fleischmann |
| 6,203,563 B1 | 3/2001 | Fernandez |
| 6,206,931 B1 | 3/2001 | Cook et al. ................. 623/23.75 |
| 6,207,875 B1 | 3/2001 | Lindqvist et al. |
| 6,213,965 B1 | 4/2001 | Augustine et al. |
| 6,213,966 B1 | 4/2001 | Augustine |
| 6,217,535 B1 | 4/2001 | Augustine |
| 6,235,009 B1 | 5/2001 | Skow |
| 6,235,047 B1 | 5/2001 | Augustine et al. |
| 6,241,697 B1 | 6/2001 | Augustine |
| 6,241,698 B1 | 6/2001 | Augustine |
| 6,241,747 B1 | 6/2001 | Ruff ................................ 606/216 |
| 6,244,311 B1 | 6/2001 | Hand et al. |
| 6,248,084 B1 | 6/2001 | Augustine et al. |
| 6,254,557 B1 | 7/2001 | Augustine et al. |
| 6,254,580 B1 | 7/2001 | Svedman |
| 6,259,067 B1 | 7/2001 | Faries, Jr. et al. |
| 6,264,622 B1 | 7/2001 | Augustine |
| 6,264,979 B1 | 7/2001 | Svedman |
| 6,267,740 B1 | 7/2001 | Augustine et al. |
| 6,283,931 B1 | 9/2001 | Augustine |
| 6,284,941 B1 | 9/2001 | Cox et al. |
| 6,287,316 B1 | 9/2001 | Agarwal et al. ............... 606/151 |
| 6,290,685 B1 | 9/2001 | Insley et al. |
| 6,293,917 B1 | 9/2001 | Augustine et al. |
| 6,325,798 B1 | 12/2001 | Edwards et al. ................. 606/41 |
| 6,345,623 B1 | 2/2002 | Heaton et al. |
| 6,364,853 B1 | 4/2002 | French et al. .................... 604/35 |
| 6,394,142 B1 | 5/2002 | Woelfel et al. ................. 138/115 |
| 6,398,767 B1 | 6/2002 | Fleischmann |
| 6,410,427 B1 | 6/2002 | Hu .................................. 438/655 |
| 6,440,427 B1 | 8/2002 | Wadström ..................... 424/400 |
| 6,458,109 B1 | 10/2002 | Henley et al. |
| 6,471,685 B1 | 10/2002 | Johnson |
| 6,472,581 B1 | 10/2002 | Muramatsu et al. ............ 602/41 |
| 6,488,643 B1 | 12/2002 | Tumey et al. ................... 602/13 |
| 6,491,682 B2 | 12/2002 | Paderni |
| 6,491,693 B1 | 12/2002 | Lytinas |
| 6,493,568 B1 | 12/2002 | Bell et al. ....................... 600/323 |
| 6,500,112 B1 | 12/2002 | Khouri |
| 6,520,982 B1 | 2/2003 | Boynton et al. |
| 6,553,998 B2 | 4/2003 | Heaton et al. |
| 6,557,704 B1 | 5/2003 | Randolph |
| 6,559,773 B1 | 5/2003 | Berry |
| 6,599,277 B2 | 7/2003 | Neubert |
| 6,626,891 B2 | 9/2003 | Ohmstede |
| 6,638,270 B2 | 10/2003 | Johnson |
| 6,648,862 B2 | 11/2003 | Watson |
| 6,663,349 B1 | 12/2003 | Discenzo et al. |
| 6,685,681 B2 | 2/2004 | Lockwood et al. |
| 6,691,047 B1 | 2/2004 | Fredericks |
| 6,695,823 B1 | 2/2004 | Lina et al. |
| 6,695,824 B2 | 2/2004 | Howard et al. |
| 6,719,779 B2 | 4/2004 | Daoud |
| 6,749,592 B2 | 6/2004 | Lord |
| 6,752,794 B2 | 6/2004 | Lockwood et al. |
| 6,755,807 B2 * | 6/2004 | Risk et al. ...................... 604/319 |
| 6,764,462 B2 | 7/2004 | Petrosenko et al. |
| 6,767,334 B1 | 7/2004 | Randolph |
| 6,800,074 B2 | 10/2004 | Henley et al. |
| 6,814,079 B2 | 11/2004 | Heaton et al. |
| 6,824,533 B2 | 11/2004 | Risk et al. |
| 6,855,135 B2 | 2/2005 | Lockwood et al. |
| 6,856,821 B2 | 2/2005 | Johnson |
| 6,936,037 B2 | 8/2005 | Bubb et al. |
| 6,951,553 B2 | 10/2005 | Bubb et al. |
| 6,966,889 B2 | 11/2005 | Saab .......................... 604/96.01 |
| 6,979,324 B2 | 12/2005 | Bybordi et al. |
| 6,994,702 B1 | 2/2006 | Johnson |
| 7,004,915 B2 | 2/2006 | Boynton et al. |
| 7,022,113 B2 | 4/2006 | Risk et al. |
| 7,070,584 B2 | 7/2006 | Johnson et al. |
| 7,077,832 B2 | 7/2006 | Fleischmann |
| 7,108,683 B2 | 9/2006 | Zamierowski |
| 7,117,869 B2 | 10/2006 | Heaton et al. |
| 7,128,735 B2 | 10/2006 | Weston |
| 7,144,390 B1 | 12/2006 | Hannigan et al. |
| 7,195,624 B2 | 3/2007 | Lockwood et al. |
| 7,245,291 B2 | 7/2007 | Sharif et al. |
| 7,276,051 B1 | 10/2007 | Henley et al. |
| 7,338,482 B2 | 3/2008 | Lockwood et al. ........... 604/543 |
| 7,381,211 B2 | 6/2008 | Zamierowski ................ 606/215 |
| 7,422,576 B2 | 9/2008 | Boynton et al. ............... 607/104 |
| 7,524,286 B2 | 4/2009 | Johnson ......................... 600/309 |
| 7,534,927 B2 | 5/2009 | Lockwood et al. ............. 602/46 |
| 2001/0029956 A1 | 10/2001 | Argenta et al. |
| 2001/0034499 A1 | 10/2001 | Sessions et al. |
| 2001/0043943 A1 | 11/2001 | Coffey |
| 2001/0052681 A1 | 12/2001 | Deavila ...................... 280/47.19 |
| 2002/0065494 A1 | 5/2002 | Lockwood et al. |
| 2002/0077661 A1 | 6/2002 | Saadat ........................... 606/221 |
| 2002/0082567 A1 | 6/2002 | Lockwood et al. ............ 604/313 |
| 2002/0082668 A1 | 6/2002 | Ingman |
| 2002/0085952 A1 | 7/2002 | Ellingboe et al. ................ 422/45 |
| 2002/0115951 A1 | 8/2002 | Norstrem et al. ................ 602/27 |
| 2002/0115952 A1 | 8/2002 | Johnson et al. |
| 2002/0120185 A1 | 8/2002 | Johnson ......................... 600/345 |
| 2002/0143286 A1 | 10/2002 | Tumey |
| 2002/0161317 A1 | 10/2002 | Risk et al. |
| 2002/0183702 A1 | 12/2002 | Henley et al. ................. 604/305 |
| 2002/0193723 A1 | 12/2002 | Batdorf, Sr. et al. |
| 2003/0032951 A1 | 2/2003 | Rittman, III et al. |
| 2003/0077311 A1 | 4/2003 | Vyakarnam et al. ............ 435/41 |
| 2003/0093041 A1 | 5/2003 | Risk et al. |
| 2003/0143352 A1 | 7/2003 | Yang et al. .................... 428/36.9 |

| | | | | | | |
|---|---|---|---|---|---|---|
| 2003/0208149 A1 | 11/2003 | Coffey | EP | 1 018 967 B1 | 8/2004 | |
| 2003/0219469 A1 | 11/2003 | Johnson et al. | EP | 1726276 | 11/2006 | |
| 2003/0225441 A1 | 12/2003 | Boynton et al. | FR | 500253 | 3/1920 | |
| 2004/0039415 A1 | 2/2004 | Zamierowski | FR | 1303238 | 7/1962 | |
| 2004/0064111 A1 | 4/2004 | Lockwood et al. | GB | 3090 | 6/1902 | |
| 2004/0167482 A1 | 8/2004 | Watson | GB | 641061 | 8/1950 | |
| 2004/0225208 A1 | 11/2004 | Johnson | GB | 692578 | 6/1953 | |
| 2004/0243073 A1 | 12/2004 | Lockwood et al. | GB | 1549756 | 8/1979 | |
| 2004/0249353 A1 | 12/2004 | Risks, Jr. et al. | GB | 1584772 | 2/1981 | |
| 2004/0260230 A1 | 12/2004 | Randolph | GB | 2195255 A | 4/1988 | |
| 2005/0004534 A1 | 1/2005 | Lockwood et al. | GB | 2197789 A | 6/1988 | |
| 2005/0010153 A1 | 1/2005 | Lockwood et al. | GB | 2220357 A | 1/1990 | |
| 2005/0033197 A1 | 2/2005 | Cottler | GB | 2235877 A | 3/1991 | |
| 2005/0065484 A1 | 3/2005 | Watson, Jr. | GB | 2307180 | 5/1997 | |
| 2005/0070858 A1 | 3/2005 | Lockwood et al. | GB | 2329127 A | 3/1999 | |
| 2005/0085795 A1 | 4/2005 | Lockwood et al. | GB | 2333965 A | 8/1999 | |
| 2005/0090787 A1 | 4/2005 | Risk et al. | GB | 2336546 A | 10/1999 | |
| 2005/0131327 A1 | 6/2005 | Lockwood et al. | GB | 2342584 A | 4/2000 | |
| 2005/0177190 A1 | 8/2005 | Zamierowski | GB | 2344531 A | 6/2000 | |
| 2005/0182445 A1 | 8/2005 | Zamierowski | GB | 2351025 A | 12/2000 | |
| 2005/0182446 A1 | 8/2005 | DeSantis ................... 606/222 | GB | 2356148 | 5/2001 | |
| 2005/0234485 A1 | 10/2005 | Seegert et al. | HU | 199304 B | 1/1989 | |
| 2005/0234510 A1 | 10/2005 | Zamierowski | HU | 51150 | 4/1990 | |
| 2005/0240220 A1 | 10/2005 | Zamierowski | HU | 205557 B | 4/1990 | |
| 2005/0283105 A1 | 12/2005 | Heaton et al. | HU | P9006526 | 1/1993 | |
| 2006/0015087 A1 | 1/2006 | Risk et al. | HU | P9302966 | 7/1996 | |
| 2006/0029650 A1 | 2/2006 | Coffey | HU | 76351 | 8/1997 | |
| 2006/0029675 A1 | 2/2006 | Ginther | HU | 215563 B | 8/1997 | |
| 2006/0041247 A1 | 2/2006 | Petrosenko et al. | HU | 1666 | 12/1999 | |
| 2006/0079852 A1 | 4/2006 | Bubb et al. | JP | 4-129536 | 4/1992 | |
| 2006/0129137 A1 | 6/2006 | Lockwood et al. | JP | 06327761 A | 11/1994 | |
| 2006/0149170 A1 | 7/2006 | Boynton et al. | SE | 84485 | 10/1935 | |
| 2006/0149171 A1 | 7/2006 | Vogel et al. | SG | 71559 | 4/2002 | |
| 2006/0173253 A1 | 8/2006 | Ganapathy et al. | SU | 587941 | 1/1978 | |
| 2006/0189910 A1 | 8/2006 | Johnson et al. | SU | 1268175 A1 | 11/1986 | |
| 2006/0213527 A1 | 9/2006 | Argenta et al. | WO | WO 80/02182 | 10/1980 | |
| 2007/0005028 A1 | 1/2007 | Risk, Jr. et al. | WO | WO 87/04626 | 8/1987 | |
| 2007/0014837 A1 | 1/2007 | Johnson et al. | WO | WO 89/04158 | 5/1989 | |
| 2007/0021697 A1 | 1/2007 | Ginther et al. | WO | WO 90/10424 | 9/1990 | |
| 2007/0021698 A1 | 1/2007 | Fleischmann | WO | WO 90/11795 | 10/1990 | |
| 2007/0032778 A1 | 2/2007 | Heaton et al. | WO | WO 91/00718 | 1/1991 | |
| 2007/0038172 A1 | 2/2007 | Zamierowski | WO | WO9108793 A1 | 6/1991 | |
| 2007/0156104 A1 | 7/2007 | Lockwood et al. | WO | WO 91/16030 | 10/1991 | |
| 2007/0233022 A1 | 10/2007 | Henley et al. ................ 604/304 | WO | WO9212750 A1 | 8/1992 | |
| 2009/0082740 A1 | 3/2009 | Lockwood et al. ............ 602/41 | WO | WO92/19313 | 11/1992 | |
| | | | WO | WO 92/20299 | 11/1992 | |
| FOREIGN PATENT DOCUMENTS | | | WO | WO93/09715 | 3/1993 | |
| AU | 745271 | 4/1999 | WO | WO 93/09727 | 5/1993 | |
| AU | 755496 | 2/2002 | WO | WO 94/00090 | 1/1994 | |
| CA | 1127488 | 7/1982 | WO | WO 94/20041 | 9/1994 | |
| CA | 2005436 | 6/1990 | WO | WO 96/05873 | 2/1996 | |
| CA | 2303085 | 3/1999 | WO | WO 96/15745 | 5/1996 | |
| DE | 372727 | 3/1923 | WO | WO97/18007 | 5/1997 | |
| DE | 2640413 A1 | 3/1978 | WO | WO 98/02205 | 1/1998 | |
| DE | 28 09 828 A1 | 9/1978 | WO | WO 98/38944 | 9/1998 | |
| DE | 2809828 A1 | 9/1978 | WO | WO 99/01173 | 1/1999 | |
| DE | 3102674 A1 | 9/1982 | WO | WO 99/13793 | 3/1999 | |
| DE | 3539533 A1 | 5/1987 | WO | WO9923990 A1 | 5/1999 | |
| DE | 40 12 232 | 10/1991 | WO | WO 99/59816 | 11/1999 | |
| DE | 4111122 A1 | 4/1993 | WO | WO 00/07653 | 2/2000 | |
| DE | 4306478 A1 | 9/1994 | WO | WO 00/15277 | 3/2000 | |
| DE | 29504378 U1 | 10/1995 | WO | WO 00/21586 | 4/2000 | |
| DE | 29715634 | 11/1997 | WO | WO 00/26100 | 5/2000 | |
| DE | 19722075 C1 | 10/1998 | WO | WO 00/28890 | 5/2000 | |
| DK | 64055 | 10/1945 | WO | WO 00/30567 | 6/2000 | |
| EP | 0 100 148 A1 | 2/1984 | WO | WO 00/32247 | 6/2000 | |
| EP | 0117632 A2 | 9/1984 | WO | WO 00/38552 | 7/2000 | |
| EP | 0 161 865 A2 | 11/1985 | WO | WO 00/38755 | 7/2000 | |
| EP | 0 358 302 A2 | 3/1990 | WO | WO 00/42958 | 7/2000 | |
| EP | 0424165 A1 | 4/1991 | WO | WO 00/59418 | 10/2000 | |
| EP | 0485657 A1 | 5/1992 | WO | WO 00/59424 | 10/2000 | |
| EP | 0547496 A1 | 6/1993 | WO | WO 00/61206 | 10/2000 | |
| EP | 0853 950 A1 | 7/1998 | WO | WO 00/64394 | 11/2000 | |
| EP | 0 777 504 B1 | 10/1998 | WO | WO 96/05873 | 2/2001 | |
| EP | 0 880 953 A2 | 12/1998 | WO | WO 01/34223 A1 | 5/2001 | |
| EP | 1 088 569 A2 | 4/2001 | WO | WO 01/37922 A2 | 5/2001 | |
| EP | 1100574 | 5/2001 | WO | WO 01/49233 A1 | 7/2001 | |
| EP | 1190732 A1 * | 3/2002 | WO | WO 01/85248 | 11/2001 | |
| EP | 1190732 A2 | 3/2002 | WO | WO 01/85248 A1 | 11/2001 | |

| | | |
|---|---|---|
| WO | WO 01/89431 | 11/2001 |
| WO | WO0238091 A1 | 5/2002 |
| WO | 0243634 A2 | 6/2002 |
| WO | WO 0243634 A1 * | 6/2002 |
| WO | WO 03/005943 | 1/2003 |
| WO | WO 03/045492 | 6/2003 |
| WO | WO 03/057071 | 7/2003 |
| WO | WO 03/057307 | 7/2003 |
| WO | WO 03/101508 | 12/2003 |

OTHER PUBLICATIONS

Davydov, et al., Khirurgiia, Jun. 1990—"Pathogenic Mechanism of the Effect of Vacuum Therapy on the Course of the Wound Process" (English translation by R. McElroy Translation Co., Austin, Texas).
Davydov, et al., Vestn. Khir., Nov. 1986—"Vacuum Therapy in the Treatment of Suppurative Lactation Mastitis" (English translation by R. McElroy Translation Co., Austin, Texas).
Davydov, et al. Vestn. Khir., Oct. 1988—"Bacteriological and Cytological Evaluation of the Vacuum Therapy of Suppurative Wounds" (English. translation by R. McElroy Translation Co., Austin, Texas).
Davydov, et al., Vestn. Khir. Mar. 1990—"Basis of the Use of Forced Early Secondary Suture in the Treatment of Suppurative Wounds by the Vacuum Therapy Method" (English translation by R. McElroy Translation Co., Austin, Texas).
Mirazimov, et al., Ortop Travmatol Protez., Oct. 1966—"Free Skin Graft of the Foot with Preparation of the Wound Surface by Vacuum Treatment" (English translation by R. McElroy Translation Co., Austin, Texas).
Borzov, et al., Vestn. Dermatol. Venerol., Aug. 1965—"Vacuum Therapy of Some Skin Diseases" (English translation by R. McElroy Translation Co., Austin, Texas).
Jeter, et al., Chronic Wound Care; 27: pp. 240-246—"Managing Draining Wounds and Fistulae: New and Established Methods".
Mulder, et al., Wound Healing Publications 1991—"Clinicians' Pocket Guide to Chronic Wound Repair".
Valenta, AIN Apr. 1994; pp. 44-45—"Using the Vacuum Dressing Alternative for Difficult Wounds".
Wolthuis, et al., Physiological Reviews Jul. 1974; vol. 54, No. 3, pp. 566-595—"Physiological Effects of Locally Applied Reduced Pressure in Man".
Fleischmann, WundForum Spezial IHW 1994; pp. 54-55—"Vacuum Sealing for Treatment of Problematical Wounds" (English translation provided).
Bucalo, et al., Wound Repair and Regeneration; Jul.-Sep. 1993; pp. 181-186—"Inhibition of Cell Proliferation by Chronic Wound Fluid".
Olenius, et al., Plastic and Reconstructive Surgery Feb. 1993: pp. 213-215—"Mitotic Activity in Expanded Human Skin".
Viljanto, et al., Br. J. Surg. 1976; vol. 63: pp. 427-430—"Local Hyperalimentation of Open Wounds".
Dunlop, et al., Br. J. Surg. May 1990; vol. 77: pp. 562-563—"Vacuum Drainage of Groin Wounds after Vascular Surgery: A Controlled Trial".
Comment-Ruckley et al., Apr. 1991, pp. 505-506 on "Vacuum Drainage of Groin Wounds after Vascular Surgery".
Landis, et al., Alternate Suction and Pressure, pp. 925-961—"The Effects of Alternative Suction and Pressure on Blood Flow to the Lower Extremities".
Morykwas, et al., Extracellular Matrix and Healing 1993; pp. 800—"Use of Negative Pressure to Increase the Rate of Granulation Tissue Formation in Chronic Open Wounds".
Svedman, et al., Annals of Plastic Surgery Aug. 1986; vol. 17, No. 2: pp. 125-133—"A Dressing System Providing Fluid Supply and Suction Drainage Used for Continuous or Intermittent Irrigation".
Schneider, et al., Plastic and Reconstructive Surgery Sep. 1998, pp. 1195-1198—"A New and Reliable Method of Securing Skin Grafts to the Difficult Recipient Bed".
Morykwas, et al., www.sma.org/soa/jsoawt97—"Nonsurgical Modalities to Enhance Healing and Care of Soft Tissue Wounds"; Feb. 11, 1999; 16 pages.
Chariker, et al., Contemporary Surgery Jun. 1989; vol. 34: pp. 59-63—"Effective Management of Incisional and Cutaneous Fistulae with Closed Suction Wound Drainage".
Tittel, et al., Eingag and Annahme des Manuskripts Jan. 7, 1987; pp. 104-107—"New Standards in Postoperative Wound Drainage".
Genecov, et al., Annals of Plastic Surgery Mar. 1998; vol. 40, No. 3: pp. 219-225—"A Controlled Subatmospheric Pressure Dressing Increases the Rate of Skin Graft Donor Site Reepithelialization".
Morykwas, et al., Annals of Plastic Surgery Jun. 1997; vol. 38, No. 6: pp. 553-562—"Vacuum-Assisted Closure: A New Method for Wound Control and Treatment: Animal Studies and Basic Foundation".
Argenta, et al., Annals of Plastic Surgery Jun. 1997; vol. 38, No. 6: pp. 563-577—"Vacuum-Assisted Closure: A New Method for Wound Control and Treatment: Clinical Experience".
Patent Application and Drawings—"The Enhancement of Wound Healing and Flap Survival by a New Negative Pressure Device", Argenta et al., consisting of 30 pages.
Nakayama, et al., Ann Plast Surg. May 1991; vol. 26, No. 5: pp. 499-502—"A New Dressing Method for Free Skin Grafting in Hands".
Medical Industry Week—article "KCI Offers New Treatment for Non-Healing Wounds"; 1 page.
Nakayama, et al., Plast Reconstr. Surg., Dec. 1990.; vol. 86, No. 6: pp. 1216-1219—"A New Method for the Dressing of Free Skin Grafts".
Sames, Br. Med. J., Nov. 5, 1977; vol. 2, No. 6096: 1123—"Sealing of Wounds with Vacuum Drainage".
Fleishmann, et al., Unfallchlrurg 1993; 96:488-492—"Vacuum Sealing for Treatment of Soft Tissue Injury in Open Fractures" (English translation of the Summary provided).
Teder, et al., J. Invest. Surg.1990; vol. 3: pp. 399-407—"Continuous Wound Irrigation in the Pig".
Wood, et al., Br. J. of Surg.1977; vol. 64: pp. 554-557—"Foam Elastomer Dressing in the Management of Open Granulating Wounds: Experience with 250 Patients".
Neumann, et al., J. of Biomed. Materials Research 1981, vol. 15: pp. 9-18—"Gelatin-Based Sprayable Foam as a Skin Substitute".
Kostluchenok et al., Vestn. Khir. Sep. 1986—"Vacuum Treatment in the Surgical Treatment of Suppurative Wounds" (English translation by R. McElroy Translation Co., Austin, Texas).
Lundvall, et al., Acta Physiol. Scand. 1989, vol. 136: pp. 403-409— "Transmission of Externally Applied Negative Pressure to the Underlying Tissue. A Study on the Upper Arm of Man".
Brochure—Aeros—Instavac Aspirator; 1 page.
Brochure—Pleur-evac Adult-Pediatric-Non-Metered Disposable "3-Bottle" Unit, A-4000; 6 pages.
Brochure—Hiblow Air Pump; 1 page.
Brochure—Aeros—Care-E-Vac; 2 pages.
One page brochure—Aeros—Moblvacll.
Brochure/Instruction Manual—Creative Medical Laboratories, Inc.—TUGS (Transportable Universal Gradient Suction) System.
Brochure—Wells Johnson Company—Point 5 Aspirator; 2 pages.
Brochure—Microtek Heritage, Inc.—The Wound-Evac ET, Closed Wound Suction System; 4 pages.
Brochure—KCI—The V.A.C. (Vacuum Assisted Closure), Nov. 5, 1998; 7 pages.
Brochure—Augustine Medical, Warm-Up Active Wound Therapy Wound Covers, 1999; 3 pages.
Brochure—Series 55—Emerson Post-Operative Suction Pumps; 1 page.
Brochure—Emerson Transport Suction Unit; 1 page.
Abdullah, BJJ, JHK Coll Radio1, Feb. 21, 2001; vol. 4, pp. 272-273—"A New Method for Fixation of Drainage Catheters".
PCT International Search Report for PCT/US02/41234 filed Dec. 20, 2002, Hill-Rom Services, Inc.
Osterbroek, R.E. et al., "A Micromachined Pressure/Flow-sensor" (Abstract only), www.ingentaconnect.com/content/els/09244247/ 1999/00000077/0000003/art00188, Sensor and Actuators A: vol. 77, No. 3, Nov. 2, 1999.
PCT International Search Report dated Jul. 11, 2003 for PCT/US03/ 17099 filed May 30, 2005.
PCT International Preliminary Examination Report dated Sep. 19, 2002 for PCT/US00/42333 filed Nov. 29, 2000.
PCT Written Opinion dated Jun. 24, 2002 for PCT/US00/42333 filed Nov. 29, 2000.

PCT International Search dated Mar. 8, 2001 for PCT/US00/42333 filed Nov. 29, 2000.
European office action dated Dec. 17, 2003 for EP Appln. No. 00991498.7-2310.
European office action dated Jan. 2, 2006 for EP Appln. No. 00991498.7-2310.
Canadian office action dated Jul. 20, 2007 for CA Appln. No. 2390131.
U.S. office action dated May 5, 2006 for U.S. Appl. No. 10/997,612, filed Nov. 24, 2004.
U.S. office action dated Oct. 31, 2006 for U.S. Appl. No. 10/997,612, filed Nov. 24, 2004.
U.S. office action dated Nov. 19, 2007 for U.S. Appl. No. 10/997,612, filed Nov. 24, 2004.
European Supplementary Search Report for EP02794397 dated Jan. 29, 2009 (2 pages).
"Jump-Start Wound Healing with Oasis," *Wounds*, Special Supplement, 13(2):1-28, 2001.
"Oasis™ Wound Dressing," *SIS™ Technology*, pp. 1-4, Sep. 2001.
"Surgisis™ Soft-Tissue Graft," *SIS™ Technology*, pp. 1-4, Sep. 2001.
Arnljots and Svedman, "Irrigation Treatment in Split-Thickness Skin Grafting of Intractable Leg Ulcers," *Scand J. Plast Reconstr. Surg.*, 19(2):211-213, 1985.
Bagautdinov, "Variant of external vacuum aspiration in the treatment of purulent diseases of soft tissues," *Current Problems in Modern Clinical Surgery: Interdepartmental Collection*, edited by V. Ye Volkov et al. (Chuvashia State University, Cheboksary, U.S.S.R. 1986);pp. 94-96 (certified translation).
Blackburn II et al.; "Negative-pressure dressings as a bolster for skin grafts," *Annals of Plastic Surgery*, 40(5):453-457, 1998.
Brochure—"Cavi-Care," *Smith & Nephew*, 2000.
Brochure—Healthpoint® Oasis® Wound Matrix, *Cook Biotech Incorporated*, 2003.
Chinn and Burns, "Closed wound suction drainage," *The Journal of Foot Surgery*, 24(1):76-81, 1985.
Dattilo, Jr. et al.; "Medical textiles: application of an absorbable barbed bi-directional surgical suture"; *Journal of Textile and Apparel, Technology and Management*, 2(2):1-5, 2002.
Davydov et al., "Concepts for the clinical-biological management of the wound process in the treatment of purulent wounds by means of vacuum therapy," *Vestnik Khirurgi*, pp. 132-136 (and 8 page English translation thereof), Jul. 1980.
Egnell Minor, Instruction Book, First Edition, 300, 7502, pp. 24, Feb. 1975.
Egnell Minor: Addition to the Users Manual Concerning Overflow Protection—Concerns all Egnell Pumps, Feb. 3, 1983, pp. 2.
Fourth SIS-ECM Symposium, Phoenix, Arizona, Dec. 6-7, 2002.
Greer et al., "The use of subatmospheric pressure dressing therapy to close lymphocutaneous fistulas of the groin," *British Journal of Plastic Surgery*, 53(6):484-487, 2000.
Johnson, "An improved technique for skin graft placement using a suction drain," *Surgery, Gynecology, and Obstetrics*, 159(6):584-585, 1984.
Klein, "Cook Incorporated forms dedicated tissue engineered products group," *PR Newswire*, 2000.
Kuznetsov and Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92, Oct. 1986.
Letsou et al., "Stimulation of adenylate cyclase activity in cultured endothelial cells subjected to cyclic stretch," *Journal of Cardiovascular Surgery*, 31:634-639, 1990.
Letter and Memo reporting Office Action issued in Mexican Application No. PA/a/2001/001124, mailed Jul. 13, 2004.
Masters, "Reliable, inexpensive and simple suction dressings," Letter to the Editor, *British Journal of Plastic Surgery*, Elsevier Science/The British Association of Plastic Surgeons, UK, 51(3):267, 1998.
McCarty, "Cook Incorporated forms dedicated tissue engineered products group," *Cook® Online, News and Media Information*, 2000.
Mendez-Eastman, "When wounds won't heal," *RN*, 61(1):20-24, 1998.

Meyer and V. Schrnieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.
Office Action issued in Australian Application No. 5255/99, mailed Aug. 6, 2002.
Office Action issued in Canadian Application No. 2,338,443, mailed Feb. 7, 2006.
Office Action issued in Canadian Application No. 2,467,837, mailed May 27, 2009.
Office Action issued in Canadian Application No. 2,481,016, mailed Aug. 13, 2009.
Office Action issued in Czech Republic Application No. PV2001-497, mailed Feb. 7, 2001.
Office Action issued in European Application No. 01998292.5, mailed Feb. 18, 2005.
Office Action issued in European Application No. 01998292.5, mailed Jul. 17, 2006.
Office Action issued in European Application No. 01998292.5, mailed Sep. 12, 2008.
Office Action issued in European Application Action No. 02784588.2, mailed Sep. 15, 2005.
Office Action issued in European Application No. 08010957.2, mailed Apr. 8, 2009.
Office Action issued in European Application No. 99 937 799, mailed Aug. 18, 2003.
Office Action issued in Japanese Application No. 2004-508861, mailed Apr. 14, 2009, and English language translation thereof.
Office Action issued in Polish Application No. P-357 417, mailed Nov. 25, 2008; English translation.
Office Action issued in Polish Application No. P-364 754, 2006.
Office Action issued in U.S. Application No. 09/369,113, mailed Jan. 31, 2001.
Office Action issued in U.S. Appl. No. 09/725,352, mailed Dec. 12, 2002.
Office Action issued in U.S. Appl. No. 09/743,737, mailed Aug. 11, 2006.
Office Action issued in U.S. Appl. No. 09/743,737, mailed Apr. 1, 2003.
Office Action issued in U.S. Appl. No. 09/743,737, mailed Jun. 19, 2002.
Office Action issued in U.S. Appl. No. 09/743,737, mailed Oct. 23, 2002.
Office Action issued in U.S. Appl. No. 09/743,737, mailed Sep. 8, 2005.
Office Action issued in U.S. Appl. No. 09/855,287, mailed Dec. 15, 2003.
Office Action issued in U.S. Appl. No. 09/855,287, mailed Jul. 14, 2005.
Office Action issued in U.S. Appl. No. 09/855,287, mailed Jun. 24, 2004.
Office Action issued in U.S. Appl. No. 09/855,287, mailed Oct. 1, 2002.
Office Action issued in U.S. Appl. No. 09/994,537, mailed Jan. 16, 2003.
Office Action issued in U.S. Appl. No. 09/994,537, mailed Jun. 30, 2003.
Office Action issued in U.S. Appl. No. 10/144,504, mailed May 14, 2004.
Office Action issued in U.S. Appl. No. 10/267,358, mailed Jun. 29, 2005.
Office Action issued in U.S. Appl. No. 10/276,778, mailed Aug. 7, 2008.
Office Action issued in U.S. Appl. No. 10/276,778, mailed Apr. 24, 2006.
Office Action issued in U.S. Appl. No. 10/276,778, mailed Jul. 13, 2007.
Office Action issued in U.S. Appl. No. 10/276,778, mailed Mar. 22, 2007.
Office Action issued in U.S. Appl. No. 10/276,778, mailed Nov. 19, 2007.
Office Action issued in U.S. Appl. No. 10/276,778, mailed Oct. 11, 2006.

Office Action issued in U.S. Appl. No. 10/496,360, mailed Jun. 2, 2009.
Office Action issued in U.S. Appl. No. 10/496,360, mailed Jun. 12, 2006.
Office Action issued in U.S. Appl. No. 10/496,360, mailed Mar. 26, 2008.
Office Action issued in U.S. Appl. No. 10/496,360, mailed Mar. 14, 2007.
Office Action issued in U.S. Appl. No. 10/496,360, mailed Oct. 3, 2008.
Office Action issued in U.S. Appl. No. 10/496,360, mailed Oct. 5, 2006.
Office Action issued in U.S. Appl. No. 10/496,360, mailed Sep. 10, 2007.
Office Action issued in U.S. Appl. No. 10/496,623, mailed Jun. 9, 2006.
Office Action issued in U.S. Appl. No. 10/509,137, mailed Dec. 20, 2007.
Office Action issued in U.S. Appl. No. 10/509,137, mailed Jun. 3, 2009.
Office Action issued in U.S. Appl. No. 10/509,137, mailed Jun. 22, 2007.
Office Action issued in U.S. Appl. No. 10/509,137, mailed Jan. 10, 2007.
Office Action issued in U.S. Appl. No. 10/509,137, mailed Nov. 24, 2008.
Office Action issued in U.S. Appl. No. 10/664,535, mailed Apr. 17, 2008.
Office Action issued in U.S. Appl. No. 10/664,535, mailed Apr. 2, 2007.
Office Action issued in U.S. Appl. No. 10/664,535, mailed Mar. 1, 2006.
Office Action issued in U.S. Appl. No. 10/664,535, mailed Oct. 26, 2007.
Office Action issued in U.S. Appl. No. 10/664,535, mailed Oct. 16, 2006.
Office Action issued in U.S. Appl. No. 10/885,431, mailed Apr. 15, 2008.
Office Action issued in U.S. Appl. No. 10/885,431, mailed Jun. 24, 2009.
Office Action issued in U.S. Appl. No. 10/885,431, mailed Mar. 22, 2007.
Office Action issued in U.S. Appl. No. 10/885,431, mailed Sep. 26, 2008.
Office Action issued in U.S. Appl. No. 10/885,431, mailed Sep. 19, 2007.
Office Action issued in U.S. Appl. No. 10/885,431, mailed Sep. 11, 2006.
Office Action issued in U.S. Appl. No. 10/997,612, mailed Apr. 30, 2007.
Office Action issued in U.S. Appl. No. 10/997,612, mailed Mar. 20, 2008.
Office Action issued in U.S. Appl. No. 10/997,612, mailed Nov. 14, 2008.
Office Action issued in U.S. Appl. No. 11/051,283, mailed Feb. 22, 2006.
Office Action issued in U.S. Appl. No. 11/051,283, mailed Jun. 5, 2009.
Office Action issued in U.S. Appl. No. 11/051,283, mailed Jan. 9, 2008.
Office Action issued in U.S. Appl. No. 11/051,283, mailed Mar. 22, 2007.
Office Action issued in U.S. Appl. No. 11/051,283, mailed Oct. 17, 2008.
Office Action issued in U.S. Appl. No. 11/051,283, mailed Sep. 7, 2007.
Office Action issued in U.S. Appl. No. 11/051,283, mailed Sep. 29, 2006.
Office Action issued in U.S. Appl. No. 11/051,283, mailed Sep. 7, 2005.
Office Action issued in U.S. Appl. No. 11/230,988, mailed Apr. 16, 2009.
Office Action issued in U.S. Appl. No. 11/230,988, mailed Aug. 26, 2009.
Office Action issued in U.S. Appl. No. 11/230,988, mailed Mar. 13, 2007.
Office Action issued in U.S. Appl. No. 11/230,988, mailed Mar. 26, 2008.
Office Action issued in U.S. Appl. No. 11/230,988, mailed Oct. 3, 2008.
Office Action issued in U.S. Appl. No. 11/230,988, mailed Sep. 28, 2006.
Office Action issued in U.S. Appl. No. 11/230,988, mailed Sep. 10, 2007.
Office Action issued in U.S. Appl. No. 11/242,543, mailed May 18, 2007.
Office Action issued in U.S. Appl. No. 11/242,543, mailed Oct. 20, 2006.
Office Action issued in U.S. Appl. No. 11/242,543, mailed Oct. 25, 2007.
Office Action issued in U.S. Appl. No. 11/347,073, mailed Apr. 1, 2008.
Office Action issued in U.S. Appl. No. 11/515,983, mailed May 11, 2009.
Office Action issued in U.S. Appl. No. 11/684,989, mailed Jul. 7, 2009.
Office Action issued in U.S. Appl. No. 11/684,989, mailed Nov. 18, 2008.
Office Action issued in U.S. Appl. No. 11/761,066, mailed Dec. 13, 2007.
Office Action issued in U.S. Appl. No. 11/761,066, mailed Jun. 2, 2009.
Office Action issued in U.S. Appl. No. 11/761,066, mailed Oct. 28, 2008.
Office Action issued in U.S. Appl. No. 11/761,066, mailed Sep. 25, 2007.
Orringer et al., "Management of wounds in patients with complex enterocutaneous fistulas," *Surgery, Gynecology & Obstetrics*, 165:79-80, 1987.
PCT International Preliminary Examination Report issued in International Application No. PCT/GB1996/02802, mailed Jan. 15, 1998.
PCT International Preliminary Examination Report issued in International Application No. PCT/US1999/17877, mailed Oct. 30, 2001.
PCT International Preliminary Examination Report issued in International Application No. PCT/US2000/42333, mailed Nov. 19, 2002.
PCT International Preliminary Examination Report issued in International Application No. PCT/US2001/44194, mailed Dec. 3, 2003.
PCT International Search Report issued in International Application No. PCT/GB1995/01983, mailed Nov. 23, 1995.
PCT International Search Report issued in International Application No. PCT/GB1996/02802, mailed Apr. 29, 1997.
PCT International Search Report issued in International Application No. PCT/GB1998/02713, mailed Jan. 8, 1999.
PCT International Search Report issued in International Application No. PCT/US1999/17877, mailed Oct. 27, 1999.
PCT International Search Report issued in International Application No. PCT/US2001/15611, mailed Sep. 5, 2001.
PCT International Search Report issued in International Application No. PCT/US2001/44194, mailed Dec. 9, 2002.
PCT International Search Report issued in International Application No. PCT/US2002/32221, mailed Feb. 5, 2003.
PCT International Search Report issued in International Application No. PCT/US2002/37814, mailed Apr. 7, 2003.
PCT International Search Report issued in International Application No. PCT/US2002/41210, mailed Oct. 28, 2003.
PCT International Search Report issued in International Application No. PCT/US2002/41228, mailed Jun. 30, 2003.
PCT International Search Report issued in International Application No. PCT/US2002/41229, mailed Jun. 30, 2003.
PCT International Search Report issued in International Application No. PCT/US2002/41231, mailed May 9, 2003.
PCT International Search Report issued in International Application No. PCT/US2002/41300, mailed Jul. 31, 2003.
PCT Written Opinion issued in International Application No. PCT/GB1996/02802, mailed Sep. 3, 1997.

PCT Written Opinion issued in International Application No. PCT/GB1998/02713, mailed Jun. 8, 1999.

PCT Written Opinion issued in International Application No. PCT/US1999/17877, mailed Aug. 20, 2001.

Roget's New Millenium Thesaurus, First Edition (v 1.3.1), 2007.

Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967) (certified translation).

Schein et al., "The 'Sandwich Technique' in the management of the open abdomen," *British Journal of Surgery*, 73:369-370, 1986.

Search Report issued in Hungarian Application No. P0103545, mailed Oct. 29, 2001.

Search Report issued in Hungarian Application No. P0500055, mailed May 3, 2005.

Solovev et al., "Guidelines, the method of treatment of immature external fistulas in the upper gastrointestinal tract," editor-in-chief Prov. V.I. Parahonyak, S.M. Kirov Gorky State Medical Institute, Gorky, U.S.S.R., 1987.

Solovev, Dissertation Abstract, "Treatment and prevention of suture failures after gastric resection," S.M. Kirov Gorky State Medical Institute, Gorky, U.S.S.R., 1988.

Supplementary Search Report issued in European Application No. 02794388, mailed Jun. 16, 2009.

Supplementary Search Report issued in European Application No. 02794392.7, mailed Jun. 5, 2009.

Supplementary Search Report issued in European Application No. 02794393.5, mailed Aug. 1, 2006.

Supplementary Search Report issued in European Application No. 02794394.3, mailed Apr. 6, 2009.

Supplementary Search Report issued in European Application No. 02796039.2, mailed Sep. 4, 2009.

Supplementary Search Report issued in European Application No. 07001838.7, mailed Mar. 5, 2007.

Supplementary Search Report issued in European Application No. 08010957.2, mailed Aug. 27, 2008.

Svedman, "A dressing allowing continuous treatment of a biosurface," *IRCS Medical Science: Biomedical Technology, Clinical Medicine, Surgery and Transplantation*, 7:221, 1979.

Svedman, "Irrigation treatment of leg ulcers," *The Lancet*, 2(8349):532-534, 1983.

Tennant, "The use of hypermia in the postoperative treatment of lesions of the extremities and thorax, " *Journal of the American Medical Association*, 64:1548-1549, 1915.

Tribble, "An improved sump drain-irrigation device of simple construction," *Archives of Surgery*, 105(3):511-513, 1972.

Wooding-Scott et al., "No wound is too big for resourceful nurses," *RN*, 51(12):22-25, 1988.

Yusupov et al., "Active wound drainage," *Vestnik Khirurgi*, 138(4) (and 7 page English translation thereof), 1987.

Živadinović et al., "Vacuum therapy in the treatment of peripheral blood vessels," *Timok Medical Journal*, 11:161-164 (certified translation), 1986.

Advisory Action issued in U.S. Appl. No. 10/885,431, mailed Dec. 8, 2009.

Advisory Action issued in U.S. Appl. No. 11/515,983, mailed Feb. 1, 2010.

Advisory Action issued in U.S. Appl. No. 11/761,066, mailed Feb. 16, 2010.

Decision on Appeal issued in U.S. Appl. No. 10/276,778, mailed Mar. 6, 2010.

Decision on Appeal issued in U.S. Appl. No. 11/242,543, mailed Mar. 5, 2010.

Office Action issued in U.S. Appl. No. 10/664,535, mailed Dec. 15, 2009.

Office Action issued in U.S. Appl. No. 11/051,283, mailed Feb. 25, 2010.

Office Action issued in U.S. Appl. No. 11/515,983, mailed Nov. 2, 2009.

Office Action issued in U.S. Appl. No. 11/684,989, mailed Dec. 29, 2009.

Office Action issued in U.S. Appl. No. 11/761,066, mailed Dec. 9, 2009.

Communication of Notice of Opposition issued in European Patent No. 1772160, mailed Apr. 28, 2010 and copy of Opposition.

Office Action issued in European Application No. 02 794 397.6, mailed Oct. 12, 2010.

Office Action issued in U.S. Appl. No. 11/051,283, mailed Oct. 15, 2010.

Response to Opposition submitted in European Patent No. EP 1 772 160, filed Sep. 29, 2010.

* cited by examiner

WOUND PACKING FOR PREVENTING WOUND CLOSURE

CROSS-REFERENCE TO RELATED APPLICATIONS

This application is a U.S. national counterpart application of international application serial no. PCT/US2002/041234 filed Dec. 20, 2002, which claims the benefit of U.S. provisional application Ser. No. 60/405,010 filed Aug. 21, 2002.

BACKGROUND OF THE INVENTION

The present disclosure relates to bandages for wounds, and in some instances, to bandages for use with a vacuum and/or irrigation source. Specifically, the present disclosure relates to wound packing used with vacuum bandages or other types of bandages to keep a wound from closing in an unwanted manner.

The prior art contemplates that chronic wounds may be treated by providing a vacuum in the space above the wound to promote healing. A number of prior art references teach the value of the vacuum bandage or the provision of vacuum in the space above the surface of a chronic wound.

A vacuum bandage is a bandage having a cover for sealing about the outer perimeter of the wound and under which a vacuum is established to act on the wound surface. Applying vacuum to the wound surface promotes healing of chronic wounds. Typically, suction tubes are provided for drawing exudate away from the wound and for creating a vacuum under the cover. The following U.S. patents establish the nature of vacuum treatment bandages and devices: U.S. Pat. Nos. 6,095,992, 6,080,189, 6,071,304, 5,645,081, 5,636,643, 5,358,494, 5,298,015, 4,969,880, 4,655,754, 4,569,674, 4,382,441, and 4,112,947. All of such references are incorporated herein by reference.

Further, the prior art contemplates that wounds may be treated by providing irrigation in the space above the wound. Typically, a tube is provided in communication with the wound surface of the wound at one end and with an irrigation source an another end. The fluid from the irrigation source travels through the tube to the wound surface.

Additionally, it is desirable to keep wound surfaces separated in some types of wounds. For example, after sinus surgery, certain wound surfaces should be separated to prevent closure of the wound in an unwanted manner.

SUMMARY OF THE INVENTION

The present invention comprises one or more of the following features, discussed below, or any combination thereof.

According to the present disclosure, several embodiments of wound packing for preventing wound closure in an unwanted manner are provided. In some embodiments, a vacuum bandage system is provided for use with a wound having a wound surface. The vacuum bandage system may include a wound dressing member and a wound insert. The wound dressing member may include a plurality of holes and a port in communication with the holes. The port may also be configured to be coupled to a vacuum source. The wound insert may be configured for placement within the wound between the wound surface and the wound dressing member. The wound insert may be made of a material which is not porous or foam-like.

The wound insert may be thin and flexible and may include a plurality of discrete passageways. The passageways may be in communication with the vacuum source. The passageways of the wound insert may be conduits through the wound insert or the passageways may comprise channels formed in each of a top and bottom surface of the insert.

In an illustrative embodiment, the insert is cylindrical in shape and is made of approximately 50 durometer silicone. Such an insert may have a diameter of approximately 0.0925 inch (2.35 mm).

Further according to the present disclosure, a method of treating a wound having a wound tunnel is provided. The method may include placing a non-porous wound insert within a tunneled portion of a wound and placing a wound dressing member over the wound insert so that the wound insert is positioned between a wound surface of the wound and the wound dressing member. The method further may include coupling the wound dressing member to a vacuum source, placing a sealing film over the wound dressing member for attachment to healthy skin surrounding the wound, and creating a negative pressure between the sealing film and a surface of the wound.

The wound inserts or packing disclosed herein may be used with all types of wounds and bandages. Thus, such wound packing may be used with regular bandages and/or vacuum bandages and/or irrigation bandages.

Features of the present invention will become apparent to those skilled in the art upon consideration of the following detailed description of the preferred embodiments exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
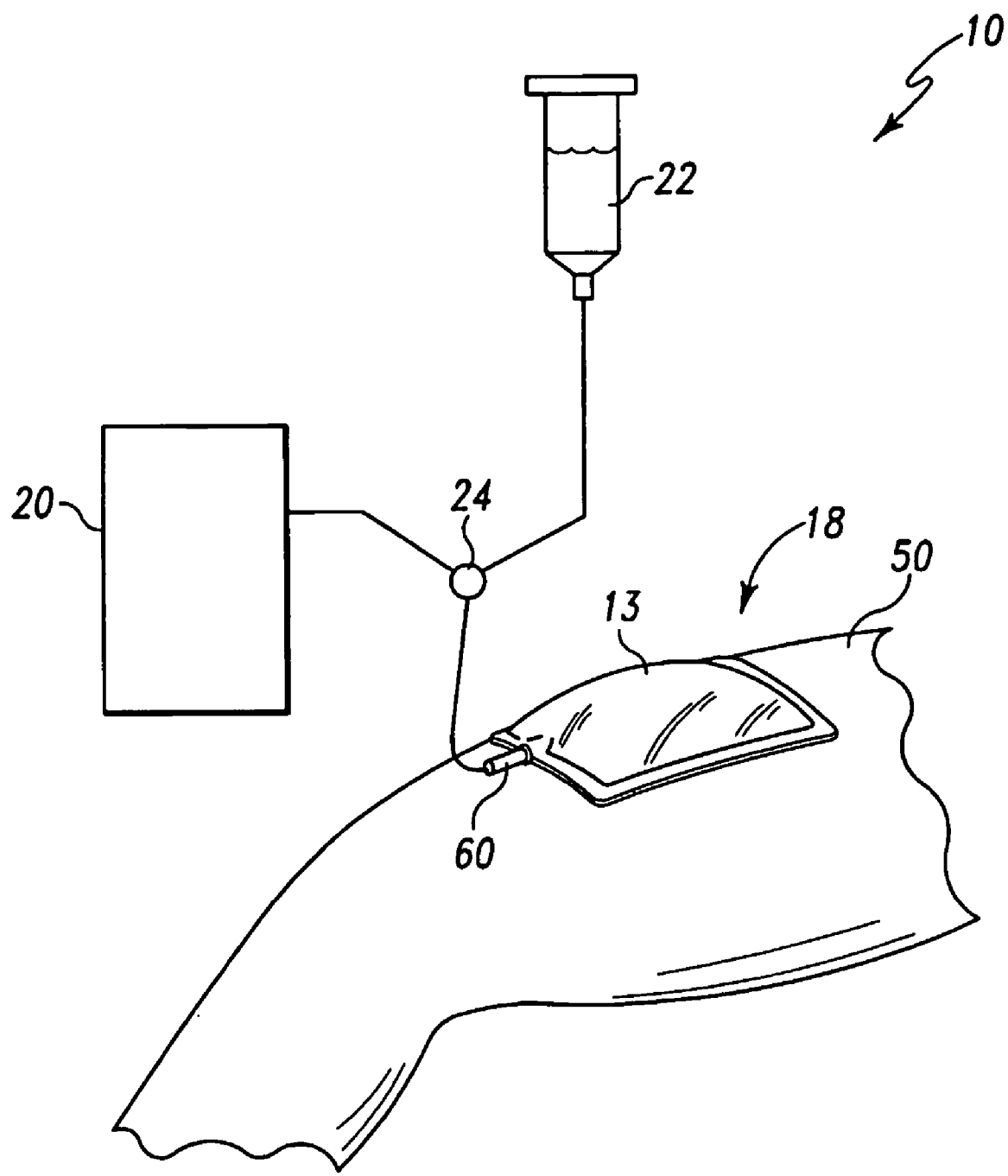
FIG. 1 is a part perspective, part diagrammatic view of a wound care bandage system showing a vacuum bandage located on the leg of a patient, and a vacuum source and an irrigation source coupled to the bandage through the use of a switch valve.
Figure 2:
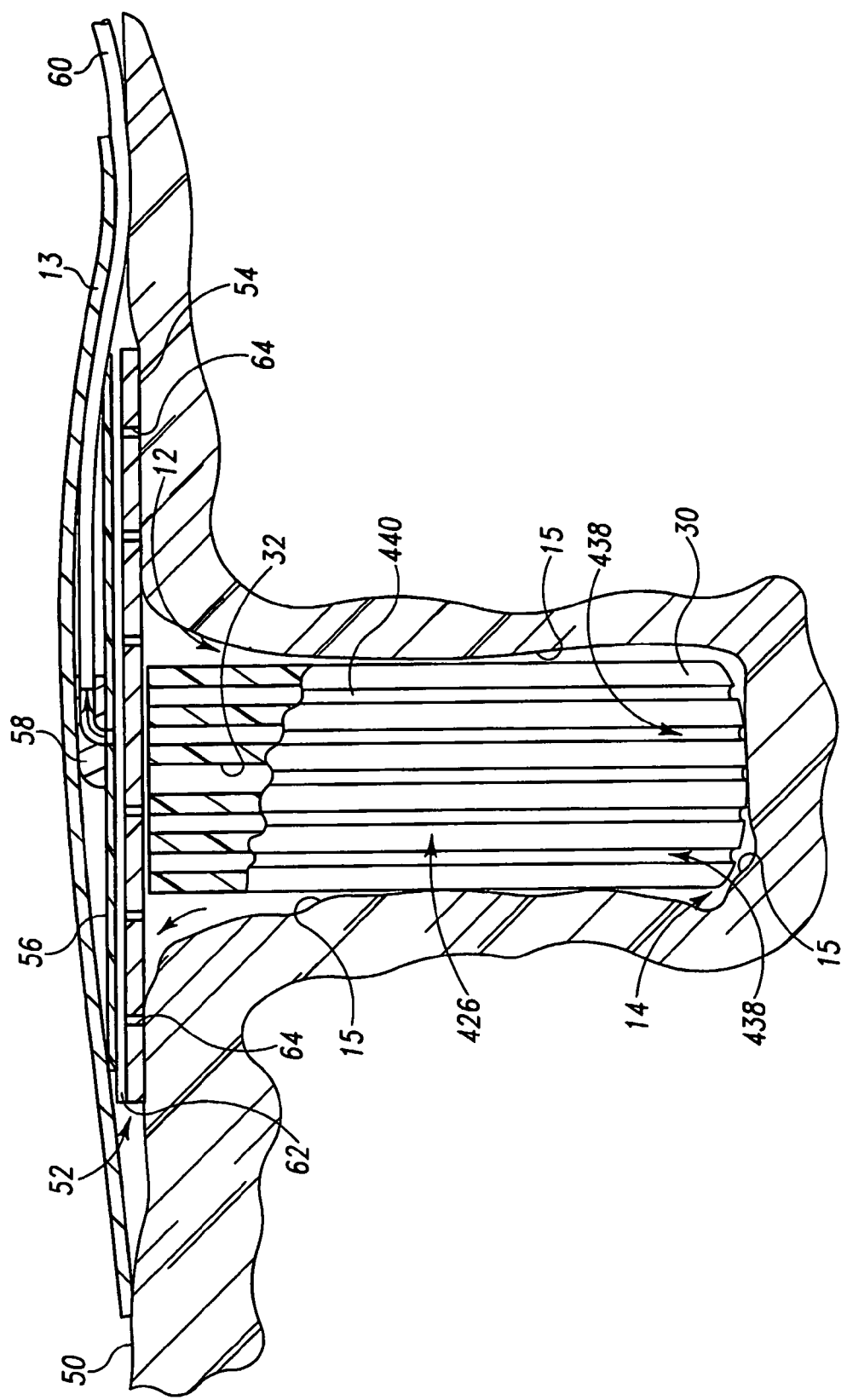
FIG. 2 is a sectional view of the vacuum bandage of the system of FIG. 1 coupled to a tunneled wound of a patient showing a wound dressing member of the system covering the tunneled wound, a tube coupling the member to the vacuum and irrigation sources (not shown), and an illustrative wound insert of the system rolled and positioned within the tunneled wound below the member to help prevent portions of the tunneled wound from prematurely healing together.
Figure 3:
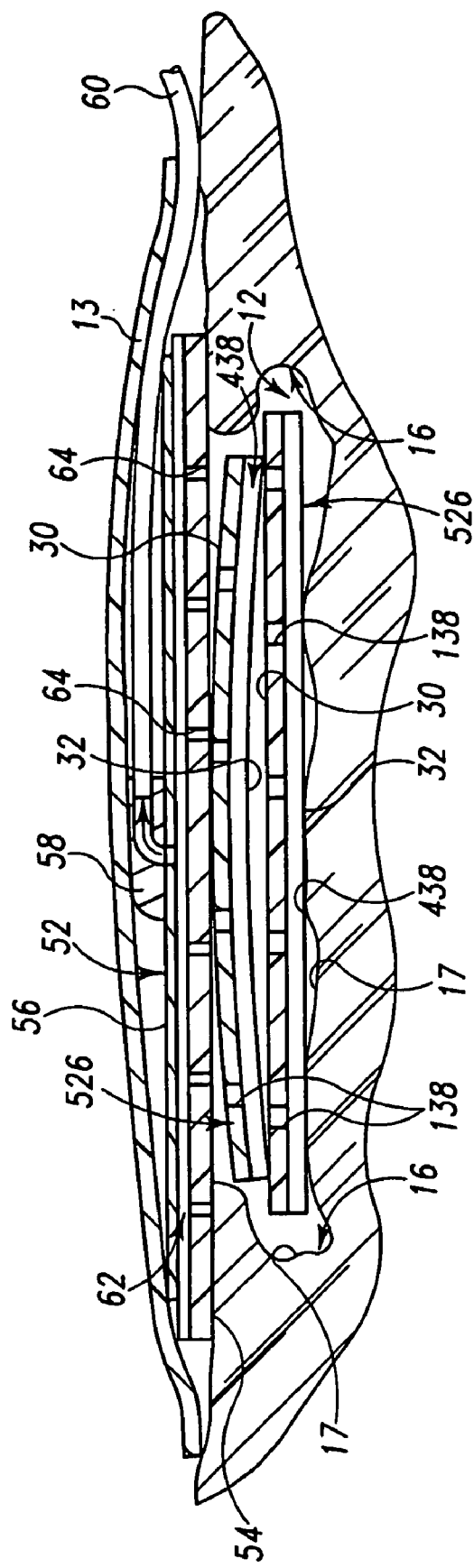
FIG. 3 is a sectional view of another illustrative vacuum bandage of the system of FIG. 1 coupled to an undermined wound of a patient showing the wound dressing member covering the undermined wound and additional illustrative wound inserts for use with the system positioned within the undermined wound.

A wound care bandage system 10 is provided for use with a wound 12, and specifically for use with a wound tunnel 14 of wound 12 (as shown in FIG. 2) and with undermined portions 16 of wound 12 (as shown in FIG. 3). As illustratively shown in FIG. 1, system 10 includes a vacuum bandage 18, a vacuum source 20 coupled to bandage 18, an irrigation source 22 coupled to bandage 18, and a valve 24 to provide selective communication between wound 12 and vacuum and irrigation sources 20, 22. System 10 further includes a wound insert or packing, illustrative embodiments of which are shown in FIGS. 4-15. Although the illustrative wound packing of FIGS. 4-15 are described herein as being used with system 10 having a vacuum source 20 and an irrigation source 22, it is within the scope of this disclosure for the wound inserts disclosed herein to be used alone or in regular bandages that do not have sources 20, 22 associated therewith or in bandages having only one or the other of sources 20, 22 associated therewith.

In some uses, wound inserts are provided to generally fill the open space created by various wound tunnels 14 and/or undermined portions 16 of wounds 12. Such wound tunnels 14 and undermined portions 16 are generally ulcerated portions of wound 12. Wound inserts help to maintain the opening created by the wound tunnels 14 and/or undermined portions 16 until the wound 12 can properly heal on its own. Further, wound inserts force the wound openings to heal generally evenly so that side and bottom surfaces 15 of wound tunnels 14 and side to bottom surfaces 17 of undermined portions 16 gradually heal toward each other to progressively shrink the open space. This may also help to prevent a "bridge" of granulations from forming across the open space and effectively sealing off an ulcerated portion of the of wound 12, thus preventing the sealed-off area from being able to be treated by the vacuum and/or irrigation of system 10.

Vacuum bandage 18, as shown in FIG. 1, is provided for use with the wound 12 and is sealed about the wound 12 by a cover or sealing film 13 of bandage 18 to create a sealed environment between the wound 12 and sealing film 13 in which a negative pressure can be established. As mentioned above, bandage 18 is selectively coupled to both vacuum source 20 and irrigation source 22 through the use of valve 24. It is within the scope of this disclosure, however, to have only a vacuum source coupled to bandage 18 or to omit both sources 20, 22.

System 10 promotes the healing of the wound 12 by providing vacuum therapy to the wound to promote blood flow and remove exudate from the wound surfaces 15, 17 of illustrative wound tunnel 14 and undermined portions 16 and by providing for irrigation of the wound 12 with fluids such as saline, for example. An illustrative wound treatment apparatus having a wound temperature control system, a medicine delivery system, and a drainage system is disclosed in U.S. Pat. No. 6,458,109. An illustrative vacuum and irrigation system is disclosed in U.S. patent Publication No. US 2002/0161317 A1. Additionally, an illustrative vacuum bandage is disclosed in U.S. patent Publication No. US 2002/0065494 A1.

Alternative vacuum bandages are disclosed in U.S. Patent Publication No. US 2002/0082567 A1. Further, a vacuum bandage system including a controller of the system is disclosed in U.S. application Ser. No. 10/159,583, filed on May 31, 2002, titled WOUND TREATMENT APPARATUS and in U.S. Application No. 60/394,970 filed on May 31, 2002, titled WOUND TREATMENT APPARATUS. All of the applications mentioned in this and the preceding paragraph are hereby incorporated herein by reference.

Figure 4:
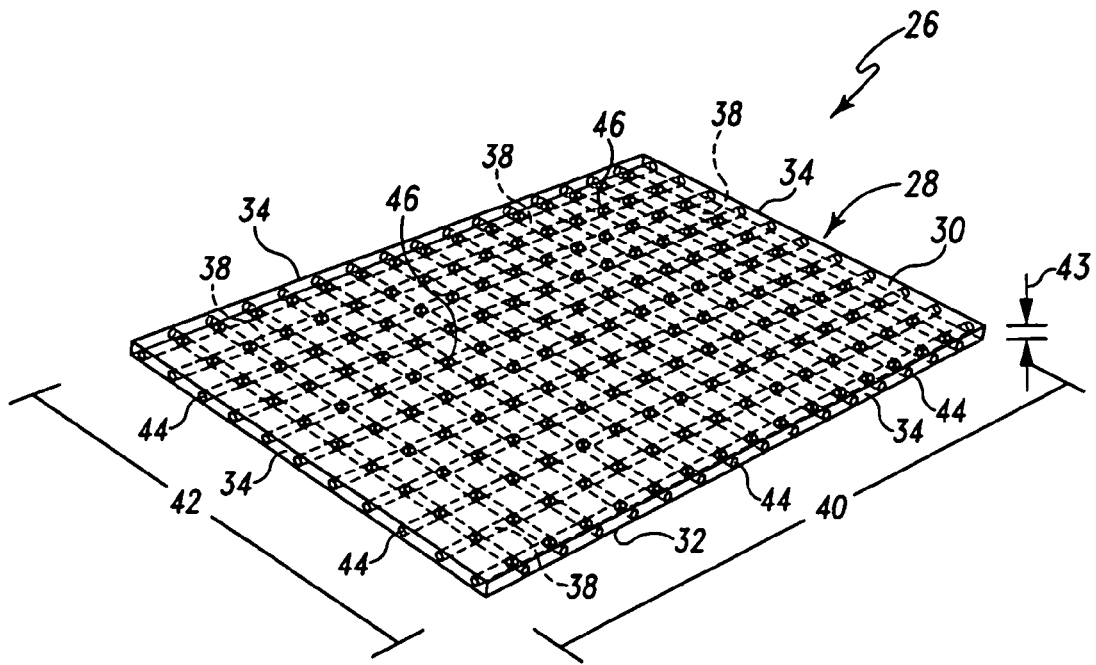
FIG. 4 is a perspective view of another illustrative wound insert showing intersecting passageways or conduits of the insert.

As shown in FIG. 4, an illustrative wound insert 26 is provided for use with system 10 and bandage 18. Wound insert 26 includes a generally thin and flexible body 28 having a top surface 30, a bottom surface 32, and side surfaces 34. Insert 26 is made of a medical grade silicone or other type of elastomer which is pliable. Two companies, for example, which manufacture such medical grade silicone are GE Silicones and NuSil Technology. It is within the scope of this disclosure, however, to include a wound insert made of any type of thin, flexible material that is non-porous, meaning that the material is generally non-foam-like. This thin, flexible material is also generally non-absorptive. For example, materials such as polyvinylchloride (PVC), PVC free of diethylhexyl phthalate (DEHP-free PVC), polyurethane, or polyethylene may be used in the manufacture of insert 26.

Further, insert 26 may be molded to include anti-microbial constituents. For example, it is within the scope of this disclosure to impregnate insert 26 with silver ions which are known anti-microbials. The following PCT publications illustrate the use of anti-microbials in various products and are incorporated herein by reference: "Antimicrobial Plastic Closures for Drinking Containers", WO 00/26100; "Antimicrobial Contact Lens Case", WO 00/038552; "Antimicrobial Fabric and Medical Graft of the Fabric", WO 00/32247; "Antimicrobial Suturing Ring for Heart Valve", WO 00/30567.

Insert 26 is also made of a generally non-adhesive material. Therefore, portions of insert 26 which may abut wound surfaces 15, 17 of wound tunnel 14 and/or undermined portions 16 of wound 12 do not adhere to the wound surfaces 15, 17. Further, insert 26 is solid in nature and generally non-compressible. For example, when a negative pressure is applied to insert 26, a thickness of insert 26 remains relatively constant.

Figure 6:
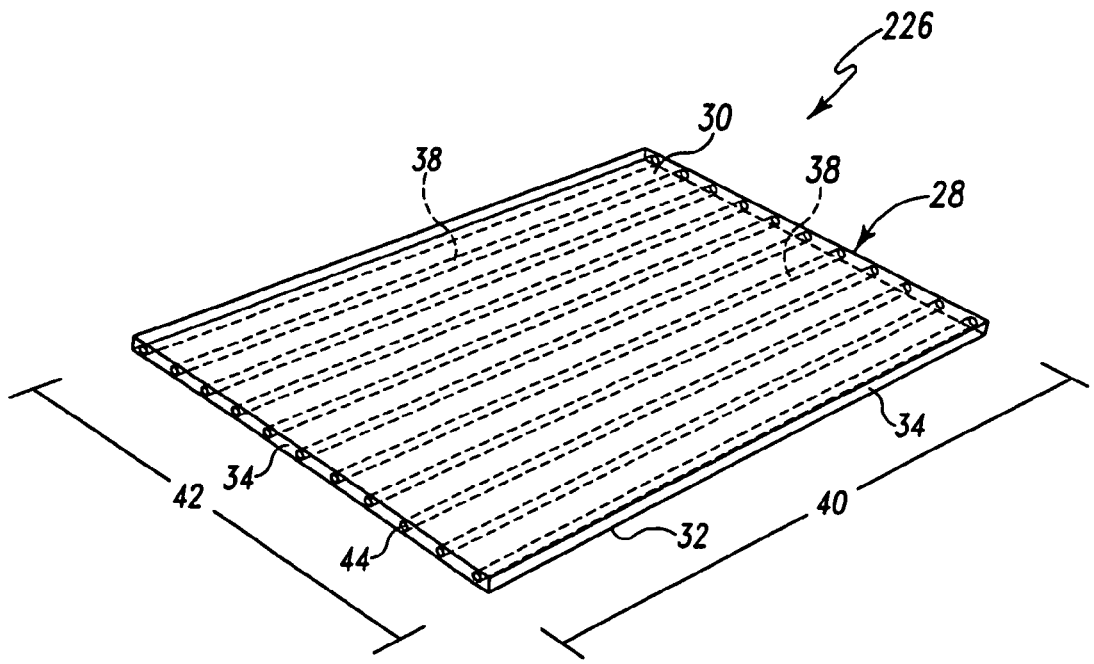
FIG. 6 is a perspective view of yet another illustrative wound insert showing internal conduits along only a length of the insert.

As shown in FIG. 4, top, bottom, and side surfaces 30, 32, 34 are generally smooth. It is within the scope of this disclosure, however, for one or more surfaces of insert 26 to be texturized or to include one or more ribs, protrusions, spacers, etc. Body 28 of insert 26 further includes passageways or conduits 38 running through body 28 along a length 40 and a width 42 of insert 26. Conduits 38 form openings 44 defined in each side surface 34 of body 28. As shown in FIG. 4, conduits 38 running along length 40 and width 42 of insert 26 lie in the same plane and therefore intersect each other at junctions 46. It is within the scope of this disclosure, however, for insert 26 to include one or more conduits 38 positioned to lie in separate planes, such as parallel planes, for example so as not to intersect. Further, it is within the scope of this disclosure for insert 26 to include any number of conduits 38 running along the length 40 and/or width 42 of insert 26. Further, conduits 38 may run along the length 40 only (as shown in FIG. 6), width 42 only, or conduits 38 may run diagonally or at any angle through body 28. Further, conduits 38 may be curved or wavy, for example, rather than generally straight as illustrated in FIG. 4.

Length 40 of illustrative insert 26 may be up to about 30 mm and width 42 of insert 26 may also be up to about 30 mm. Further, a thickness 43 of insert 26 may be within the range of about 1 mm to about 15 mm, for example. Although illustrative insert 26 has the above-mentioned dimensions, it is within the scope of this disclosure for insert 26 (an similar alternative inserts described below) to have other suitable dimensions for treating wounds and particularly for treating tunneled and/or undermined portions of wounds in a vacuum therapy system. Further, although insert 26 may be formed having certain dimensions, it is within the scope of this disclosure for a caregiver to trim insert 26 to fit a particular wound.

Figure 5:
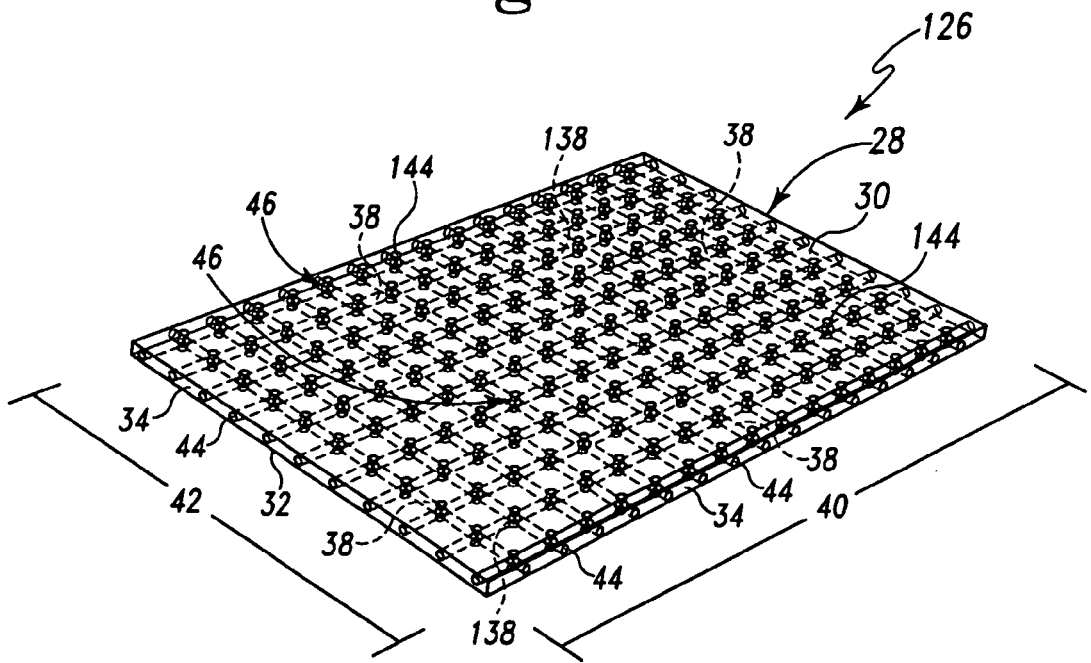
FIG. 5 is a perspective view of yet another illustrative wound insert, similar to the insert shown in FIG. 4, showing through holes located at the intersections of the internal conduits for communication with the internal conduits.

Another illustrative insert 126 is shown in FIG. 5. Insert 126 is similar to insert 26. Therefore, like reference numerals have been used for similar components or features. The only difference between insert 26 and insert 126 is that insert 126 includes generally vertical conduits or through holes 138 positioned at junctions 46 for communication with intersecting conduits 38 along the length 40 and width 42 of body 28. Conduits 138 form openings 144 defined in each of the top and bottom surfaces 30, 32 of body 28. It is also within the scope of this disclosure for conduits 138 of insert 126 to be located at areas other than junctions 46 of conduits 38.

Figure 7:
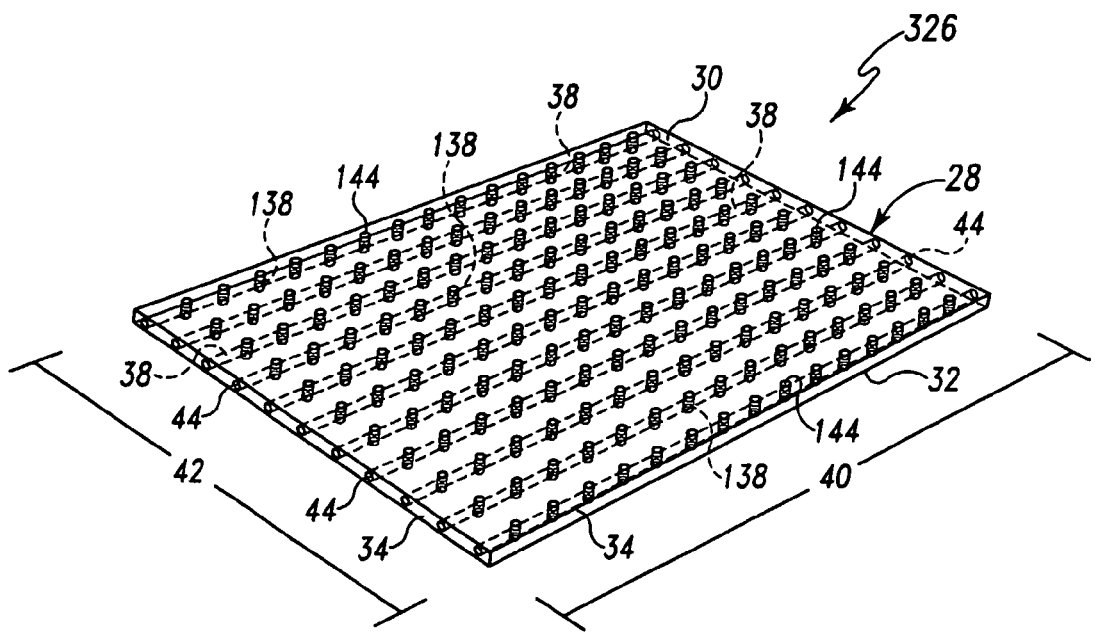
FIG. 7 is a perspective view of still another illustrative wound insert showing internal conduits along a length of the insert and through holes generally perpendicular to the conduits and in communication with the conduits.

As mentioned above, another illustrative insert 226 is provided in FIG. 6 where insert 226 includes conduits 38 only along length 40 of body 28. FIG. 7 shows yet another illustrative insert 326, similar to insert 226, and further including through holes 138 positioned at spaced apart intervals along each conduit 38. Conduits 38 run along length 40 of body 28 and each through hole 138 forms opening 144 in top and bottom surfaces 30, 32 of body 28. In alternative embodiments, through holes 138 are spaced from conduits 38.

Figure 8:
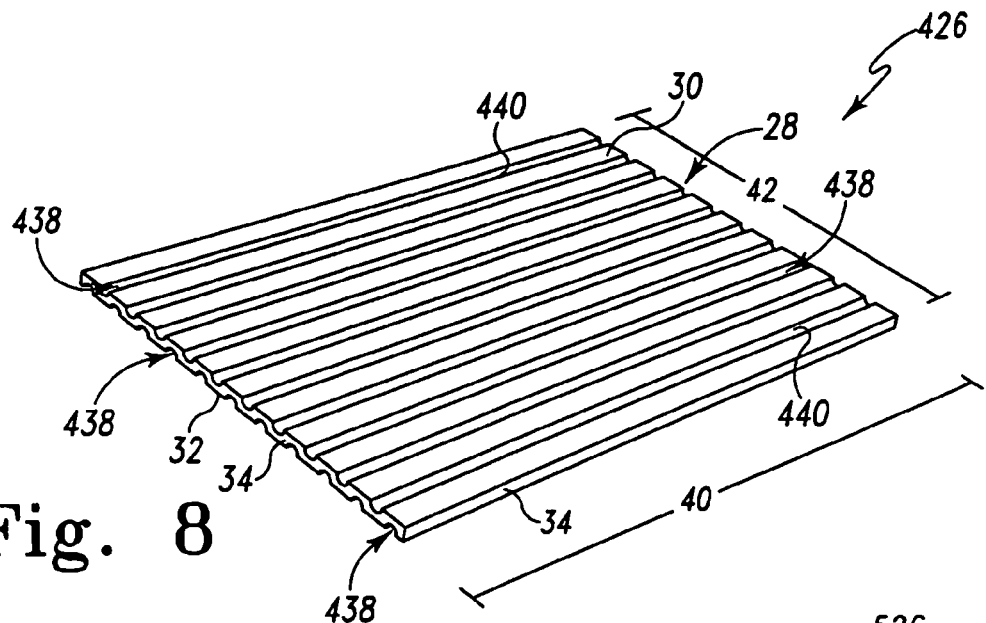
FIG. 8 is a perspective view of the wound insert of FIG. 2 showing external channels formed in both a top and bottom surface of the insert.

As shown in FIG. 8, another alternative insert 426 is provided including top, bottom, and side surfaces 30, 32, 34. Insert 426 is similar to the inserts described above, however, illustrative insert 426 does not include conduits 38 or 138. Insert 426 does include passageways or channels 438 formed in top and bottom surfaces 30, 32. Illustratively, channels 438 run along length 40 of insert 426. Further illustratively, channels 438 of top and bottom surface 30, 32 are alternately spaced along width 42 of insert 426 so that a bottom channel 438 is generally not positioned directly below a top channel 438. Illustratively, channels 438 have a generally semi-circular or curved profile and define a curved surface 440. Although illustrative channels 438 are generally straight along length 40, it is within the scope of this disclosure to include channels that are wavy, zig-zagged, etc., or channels that run at an angle to the length 40 and/or width 42 of insert 426.

Figure 9:
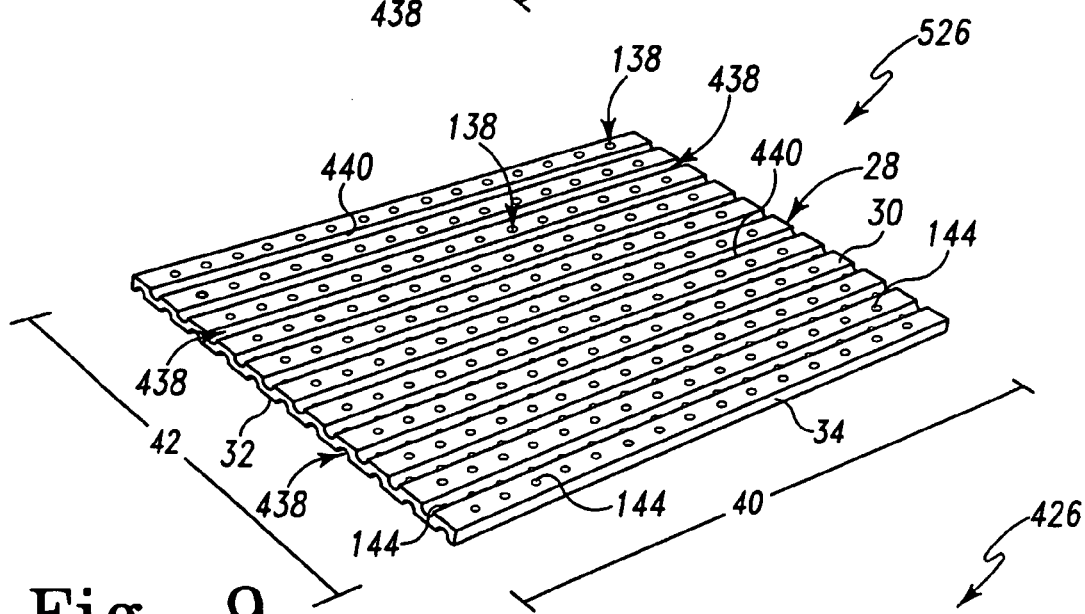
FIG. 9 is a perspective view of the wound insert of FIG. 3 showing external channels formed in top and bottom surfaces of the insert and further showing through holes in communication with the channels.

Still another alternative insert 526 is shown in FIG. 9. Insert 526 is similar to insert 426, shown in FIG. 8, however, insert 526 further includes vertical conduits or through holes 138 forming openings 144 in top and bottom surfaces 30, 32 of body 28 to communicate with channels 438 formed in each of the top and bottom surfaces 30, 32.

Figure 11:
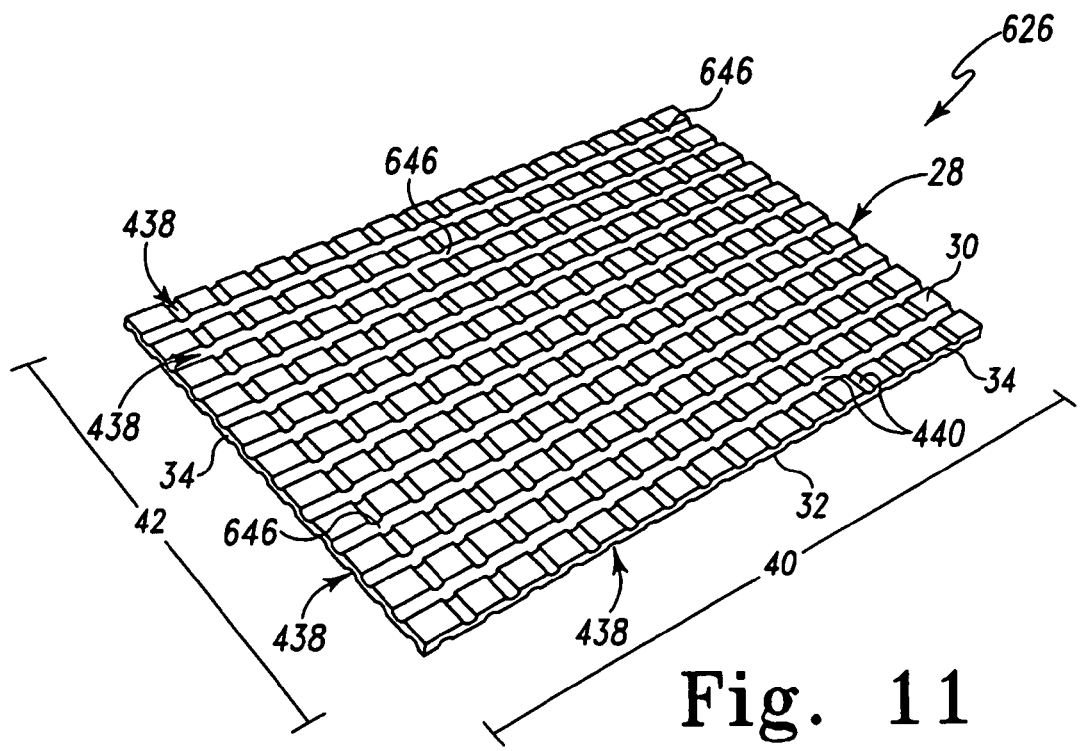
FIG. 11 is a perspective view of still another illustrative wound insert showing intersecting external channels of the insert along both a length and width of the insert.

Looking now to FIG. 11, a wound insert 626 is provided. Wound insert 626 includes both "lengthwise and widthwise" channels 438 running along the length 40 and width 42 of body 28. Each of the "lengthwise and widthwise" channels 438 is formed in top and bottom surfaces 30, 32 of body 28 and is alternately spaced thereon. The channels 438 intersect each other at junctions 646.

Figure 12:
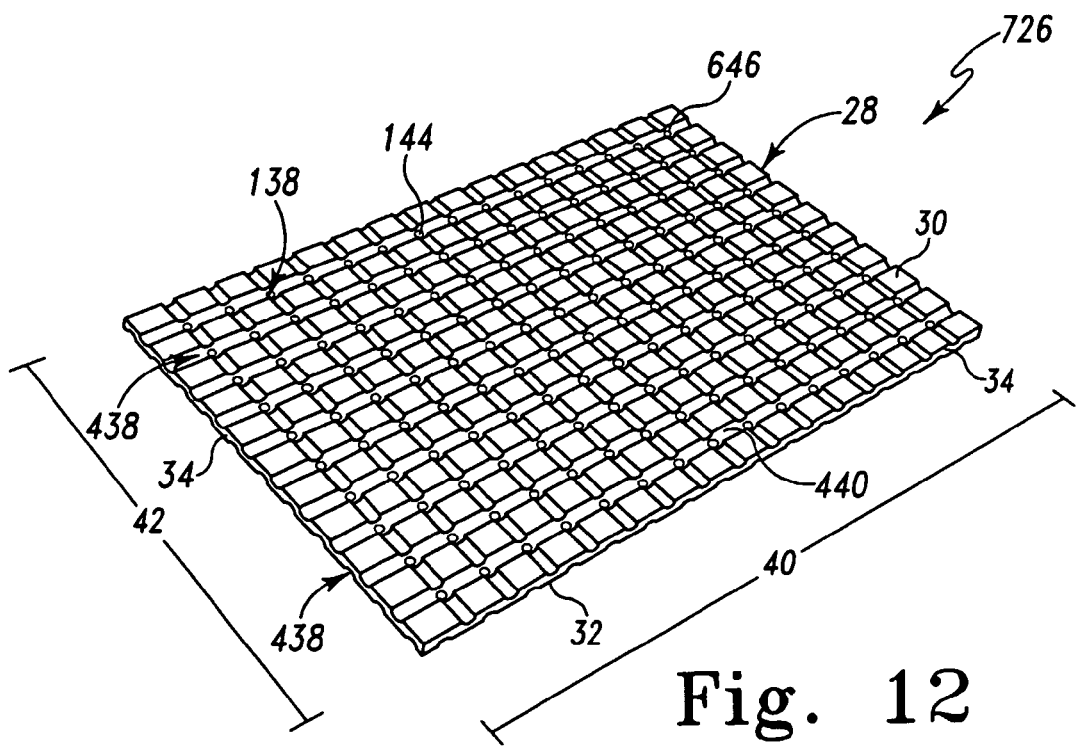
FIG. 12 is a perspective view of yet another illustrative wound insert showing intersecting external channels and through holes in communication with the channels.

Another illustrative wound insert 726 is shown in FIG. 12. Wound insert 726 includes all the features of wound insert 626 (shown in FIG. 11), such as vertical and horizontal channels 438 formed in top and bottom surfaces 30, 32 of body 28. Wound insert 726 further includes vertical conduits 138 at junctions 646 of each of the vertical and horizontal channels 438 formed in top surface 30 of body 28. It is within the scope of this disclosure to further include through holes 138 at junctions (not shown) of each of the vertical and horizontal channels 438 formed in bottom surface 32. It is further within the scope of this disclosure to include through holes 138 in communication with one or more channels 438 at areas other than junctions 646.

As is described above, various illustrative wound inserts 26, 126, 226, 326, 426, 526, 626, 726 are provided for use with a vacuum bandage or with other types of bandages or alone (i.e., without other bandage components). Illustrative inserts are all thin and flexible and generally rectangularly shaped, although, it is within the scope of this disclosure to include thin, flexible inserts of any suitable shape such as circular, triangular, oval, etc. In addition, a caregiver may trim any of the disclosed inserts to a desired shape using scissors, for example. Further, all inserts described above include passageways such as conduits 38, through holes 138, and/or channels 438. In some embodiments, the passageways are provided to communicate negative pressure from vacuum source 20, or fluid from irrigation source 22, to tunneled portions 14 or undermined portions 16 of wound 12.

Figure 13:
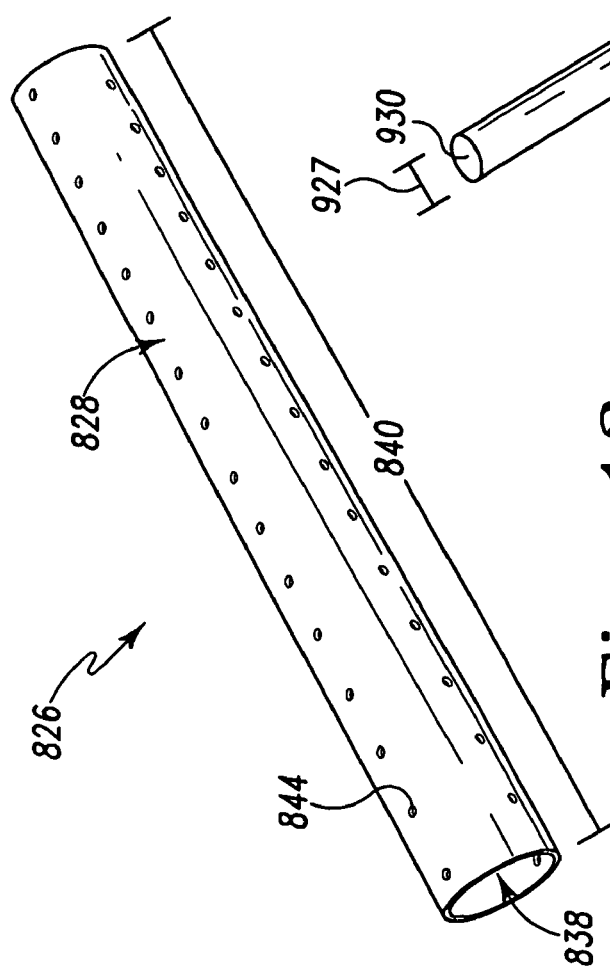
FIG. 13 is a perspective view of another illustrative wound insert being tube-shaped and including holes through a body of the insert in communication with a central passageway of the insert.

Yet another illustrative insert 826 is shown in FIG. 13. Insert 826 is made of the same thin, flexible material as the inserts described above. However, body 828 of insert 826 is formed in the shape of a hollow cylinder forming a central conduit 838 therethrough. Insert 826 includes passageways or through holes 844 formed through body 828 to communicate with central conduit 838. Illustratively, holes 844 are arranged in rows along a length 840 of insert 826. It is within the scope of this disclosure, however, for holes 844 to be arranged in any random or non-random pattern.

Figure 15:
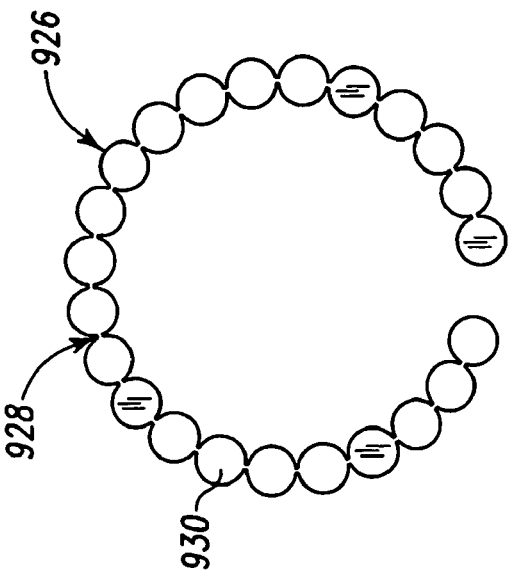
FIG. 15 is a top plan view of a group of the rod-shaped inserts of FIG. 14 as they are illustratively manufactured by extension molding, for example.
Figure 14:
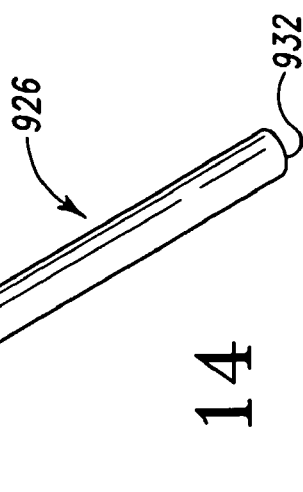
FIG. 14 is a perspective view of another illustrative wound insert showing a long, cylindrical, solid rod-shape of the insert.

Still another insert 926 is shown in FIG. 14. Illustratively, insert 926 is rod-shaped and has a generally circular profile. Each insert 926 is solid, although, it is within the scope of this disclosure to drill or otherwise form holes or passageways through insert 926. Illustratively, each insert 926 has a diameter 927 of 0.0925 inch (2.350 mm). It is within the scope of this disclosure for insert 926 to have any suitable diameter for use with tunneled wounds 14. Inserts 926 are manufactured by extruding the material into circular rods attached to each other by a small web of material 928, as shown in FIG. 15, for example. Illustratively, web 928 is 0.005 inch (0.127 mm) from rod to rod. Further, as illustratively shown in FIG. 15, twenty-three inserts 926 are extruded simultaneously. Each insert 926 is positioned at a 15° angle to adjoining inserts. Web 928 connects inserts 926 to each other to allow multiple inserts to be extruded simultaneously. Further, web 928 is sufficiently small to allow a user to separate, by pulling, for example, each insert away from the nearest adjoining insert(s).

Inserts 926 may be extruded to any suitable length. Further, a caregiver dressing a particular tunneled wound 14 may further trim inserts 926 to an appropriate length. Inserts 926 are made from the same material described above with respect to the other inserts of the present disclosure. Each insert 926 includes a cylindrical body 929, a first end 930, and a second end 932 (shown in FIG. 14). In use, multiple inserts 926 may be inserted into a tunneled wound 14 to maintain the opening of the tunneled wound 14 until the wound is able to sufficiently heal properly. Although insert 926 is primarily described herein for use with tunneled portions 14 of wound 12, it is within the scope of this disclosure to use insert 926 with undermined portions 16 of wounds 12 as well. Further, it is within the scope of this disclosure for the profile of insert 926 to be a shape other than circular, such as square-shaped, triangular, rectangular, diamond-shaped, oval-shaped, etc.

As mentioned above, wound inserts 26, 126, 226, 326, 426, 526, 626, 727, 826, 926 are provided for placement within a wound tunnel 14 and/or an undermined portion 16 of a wound 12, such as that illustrated in FIGS. 2 and 3. Specifically, FIG. 2 illustrates the use of insert 426 inserted within a wound 12 having a wound tunnel 14 extending below a surface 50 of the skin.

Figure 10:
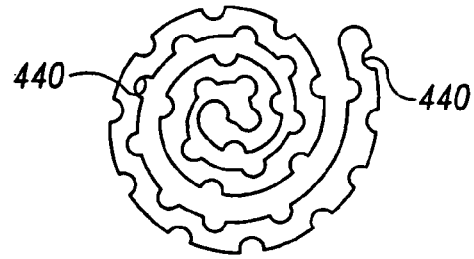
FIG. 10 is a top plan view of the wound insert shown in FIGS. 2 and 8 showing the insert rolled along its length for insertion within a wound tunnel of a wound, for example.

Generally, prior to insertion within a wound tunnel 14, for example, the thin, flat inserts 26, 126, 226, 326, 426, 526, 626, 726 are rolled along their length 40. FIG. 10 illustrates and end view of insert 426 (shown in FIG. 8) after insert 426 has been rolled along its length 40 for insertion into tunneled portion 14 of wound 12, for example. Illustratively insert 426 is inserted into wound tunnel 14 to help prevent a portion of tunnel 14 from prematurely closing or forming a bridge across the tunnel 14. Although illustrative insert 426 is inserted within tunnel 14, it is within the scope of this disclosure to place any other insert into tunneled portion 14 The inserts are provided to effectively maintain the opening created by tunnel 14 to allow tunnel 14 to heal in a more consistent and controlled manner evenly reducing the size of the tunnel 14 from the outer surfaces 15 of tunnel 14 inward until tunnel 14 has completely healed.

It is also contemplated that, in some embodiments, illustrative inserts are in communication with vacuum source 20 through vacuum bandage 18 and therefore may communicate the suction or negative pressure from vacuum source 20 along the passageways of each insert to the bottom and side walls 15 of tunnel 14. This negative pressure may help draw exudate away from wound 12. The vacuum or negative pressure which draws blood from the body to the wound surface 15 and draws exudate from the wound 12 up through the respective insert and through portions of vacuum bandage 18 promotes the healing of wound 12. As wound 12 heals, granulations form along wound surface 15. Granulations, therefore, are the replacement within the wound bed of tissue lost.

As shown in FIGS. 2 and 10, the thin, flexible, and generally flat inserts (such as inserts 26, 126, 226, 326, 426, 526, 626, 726) are rolled along their length 40 so that such inserts may be inserted within tunnel 14 to generally fill the space created by tunnel 14. FIG. 10, for example, shows an end of insert 426 (shown in FIG. 8) after having been rolled along its length 40 to form a spiral-like shape so that channels 438 are positioned to lie generally vertically when insert 426 is placed within tunnel 14, as shown in FIG. 2. Each insert 26, 126, 226, 326, 427, 526, 626, 726 may be rolled so that either the top surface 30 or the bottom surface 32 is adjacent to surfaces 15 of tunnel 14 once inserted therein. Further, it is within the scope of this disclosure to roll each insert along its width 42, or even at an angle to the length 40 and width 42, as well, so that the insert is formed into a tube-like shape insertable within tunnel 14.

Illustratively, it is not necessary for a caregiver to roll insert 826 (shown in FIG. 13) or insert 926 (shown in FIGS. 14 and 15) prior to placing either insert 826, 926 within tunnel 14 because each insert 826, 926 is already tube-like in shape. Further, it is within the scope of this disclosure for a caregiver to trim each insert to size and insert to fit the tunneled or undermined portions 14, 16 of any wound 12. As discussed above, any number of inserts 926 may be inserted within wound tunnel 14 either individually, or connected by webs 928. Further, suction and/or irrigation fluids may be communicated to a bottom portion of wound tunnel 14 by spaces created between the inserts 926 within tunnel 14.

In the treatment of undermined portions 16 of wounds 12, it may not be necessary to roll an insert into a tube-like shape as is described above with respect to tunneled portions 14 of wounds 12. As is illustratively shown in FIG. 3, undermined portions 16 of wound 12 are filled by the use of two inserts 526 (shown in FIG. 3) where one insert 526 is positioned to lie on top of the other insert 526. Although inserts 526 are shown in FIG. 3, it is within the scope of this disclosure to use any type of generally thin, flexible insert with the use of undermined or tunneled wounds. Inserts 526 generally fill a space created by undermined portions 16 of wound 12. It is also contemplated that cylindrically-shaped inserts 826 and 926 may be used to fill or pack undermined portions 16 as well.

As mentioned above, wound inserts of the present disclosure may be provided as part of vacuum bandage system 10 for use with a vacuum bandage 18 coupled to vacuum source 20. Bandage 18 may also be coupled to irrigation source 22, as shown in FIG. 1, for example. The illustrative vacuum bandage 18, shown in FIGS. 1-3 includes a wound dressing member 52 adjacent wound 12 and sealing film 13 covering member 52 and sealed about member 52 and wound 12 to the patient's healthy skin 50 surrounding wound 12.

Illustrative member 52 of bandage 18 includes a smooth wound facing surface 54. Wound facing surface 54 may also be textured or roughened and/or may include spacers, ribs, protrusions, etc., extending from surface 54. Member 52 further includes opposite surface 56. Illustrative member 50 further includes a tube connector or port 58 coupled to opposite surface 56. Connector 58 is coupled to a tube 60 of system 10 in communication with vacuum and irrigation sources 20, 22. Member 50 also includes one or more passageways 62 formed between opposite surface 56 and wound facing surface 54. Each passageway 62 is in communication with connector 58 to communicate either negative pressure from vacuum source 20 to wound 12 or to communicate fluid from irrigation source 22 to wound 12. A plurality of holes 64 are illustratively provided through wound facing surface 54. Holes 64 communicate with wound 12 and passageways 62 as well. Further illustratively, wound member 52 is made of the same material as the various wound inserts described above. Although illustrative member 52 is provided, it is within the scope of this disclosure to include a vacuum bandage having any suitable type of wound dressing member having means for communicating negative pressure and/or irrigation fluid to the wound.

Although the invention has been described in detail with reference to certain embodiments, variations to modifications exist within the scope and spirit of the invention as described and defined in the following claims.

The invention claimed is:

1. A vacuum bandage system for use with a wound having a wound surface, the vacuum bandage system comprising:
a wound dressing member made of a generally non-porous material and configured to engage at least a portion of the wound surface of the wound, the wound dressing member having a plurality of holes and a port in communication with the holes via one or more passageways formed in the wound dressing member between the port and the holes and configured to be coupled to a vacuum source,
a wound insert configured for placement within the wound between the wound surface and the wound dressing member, the insert being made of a material which is not porous or foam-like, and
a cover configured for placement over the wound dressing member such that the cover engages healthy skin surrounding the wound in order to seal about the wound and create a sealed environment between the wound and the cover in which a negative pressure can be established.

2. The vacuum bandage system of claim 1, wherein the generally non-porous material comprises medical-grade silicone.

3. The vacuum bandage system of claim 1, wherein the wound insert is thin, flexible, and includes a plurality of discrete passageways in communication with the vacuum source.

4. The vacuum bandage system of claim 3, wherein the passageways are conduits through the wound insert.

5. The vacuum bandage system of claim 4, wherein the insert includes a top surface, a bottom surface, and a side surface, and wherein the conduits form holes in the side surface, and wherein the insert further includes holes in communication with the conduits and forming holes in one or more of the top and bottom surfaces.

6. The vacuum bandage system of claim 3, wherein the insert includes a top surface and a bottom surface, and wherein the passageways comprise channels formed in each of the top and bottom surfaces.

7. The vacuum bandage system of claim 6, wherein the insert further includes holes between the channels and the top and bottom surfaces.

8. The vacuum bandage system of claim 1, wherein the insert is cylindrical in shape.

9. The vacuum bandage system of claim 8, wherein the insert is made of approximately 50 durometer silicone.

10. The vacuum bandage system of claim 8, wherein the insert has a diameter of approximately 0.0925 inch (2.35 mm).

11. A wound insert for use with a vacuum bandage having a suction tube coupled to a vacuum source and a wound dressing member coupled to a wound and including a tube port receiving the suction tube, the insert comprising:
a thin, flexible member including a plurality of discrete passageways in communication with the vacuum bandage, the thin, flexible member being spaced from the suction tube, wherein the thin, flexible member includes a top surface, a bottom surface, and side surfaces and the passageways comprise bores through the body extending from one side surface to another and bores through the body extending from the top surface to the bottom surface.

12. A wound insert for use with a vacuum bandage including a wound dressing member coupled to a wound, a port of the wound dressing member, and a tube coupled to the port and to a vacuum source, the wound insert being positioned between the vacuum bandage and a wound surface of the wound, the wound insert comprising:
a body made of a generally non-porous, flexible material, wherein the body is cylindrical in shape, wherein a height of the cylindrical body is substantially greater than a diameter of the cylindrical body, and further wherein the body includes either (i) a solid top surface and a solid bottom surface, or (ii) a single passageway along a longitudinal axis of the body which extends between and through a top end and a bottom end of the body.

13. The wound insert of claim 12, wherein the body is generally rod-shaped.

14. The wound insert of claim 12, wherein the body has a diameter of approximately 0.0925 inch (2.35 mm).

15. The wound insert of claim 12, wherein the body includes discrete passageways.

16. The wound insert of claim 12, wherein the body is made of a generally non-adhesive material.

17. The vacuum bandage system of claim 1, wherein the wound insert is configured to prevent an ulcerated portion of the wound from forming a bridge to another ulcerated portion of the wound.

18. The vacuum bandage system of claim 17, wherein the wound insert includes a rod-shaped wound insert.

19. The vacuum bandage system of claim 18, wherein the wound insert is made of a generally non-porous material.

20. The vacuum bandage system of claim 1, wherein the wound insert comprises a plurality of rods that are made of a generally non-porous, flexible material and that are held together by webs that are tearable to permit the rods to be separated from each other.

21. The wound insert of claim 12, wherein the body is hollow to define a central conduit there through.

22. The wound insert of claim 21, wherein the body further defines passageways formed through the body to communicate with the central conduit.

* * * * *